(12) United States Patent
Schmid et al.

(10) Patent No.: US 11,040,988 B2
(45) Date of Patent: *Jun. 22, 2021

(54) METHOD FOR PRODUCING AN ORGANIC ELECTRONIC COMPONENT, AND ORGANIC ELECTRONIC COMPONENT

(71) Applicant: Novaled GmbH, Dresden (DE)

(72) Inventors: Guenter Schmid, Hemhofen (DE); Anna Maltenberger, Leutenbach (DE); Sebastien Pecqueur, La Couture (FR); Stefan Regensburger, Neumarkt (DE)

(73) Assignee: NOVALED GMBH, Dresden (DE)

( * ) Notice: Subject to any disclaimer, the term of this patent is extended or adjusted under 35 U.S.C. 154(b) by 550 days.

This patent is subject to a terminal disclaimer.

(21) Appl. No.: 15/515,735

(22) PCT Filed: Dec. 22, 2014

(86) PCT No.: PCT/EP2014/079049
§ 371 (c)(1),
(2) Date: Mar. 30, 2017

(87) PCT Pub. No.: WO2016/050330
PCT Pub. Date: Apr. 7, 2016

(65) Prior Publication Data
US 2017/0317288 A1 Nov. 2, 2017

(30) Foreign Application Priority Data
Sep. 30, 2014 (DE) .......................... 102014114231.4

(51) Int. Cl.
*C07F 1/08* (2006.01)
*H01L 51/00* (2006.01)
(Continued)

(52) U.S. Cl.
CPC .................. *C07F 1/08* (2013.01); *C07F 9/94* (2013.01); *H01L 21/0212* (2013.01);
(Continued)

(58) Field of Classification Search
CPC ........................... H01L 21/0212; C07C 63/06
See application file for complete search history.

(56) References Cited

U.S. PATENT DOCUMENTS 4,622,355 A 11/1986 Arnold, Jr. et al.
5,247,226 A 9/1993 Sato et al.
(Continued)

FOREIGN PATENT DOCUMENTS

CN 102576802 A 7/2012
CN 103493236 A 1/2014
(Continued)

OTHER PUBLICATIONS

Pecqueur, S., "Lewis Acid-Base Theory Applied on Evaluation of New Dopants for Organic Light-Emitting Diodes," Als Dissertation genehmigt, von der Technischen Fakultät der, Friedrich-Alexander-Universität Erlangen-Nürnberg, Aug. 12, 2014, pp. 1-178.
(Continued)

*Primary Examiner* — Robert A Vetere
(74) *Attorney, Agent, or Firm* — Slater Matsil, LLP

(57) ABSTRACT

A method for producing an organic electronic component and an organic electronic component are disclosed. In an embodiment the component comprises at least one organic electronic layer having a matrix, wherein the matrix contains a metal complex as a dopant, wherein the metal complex comprises at least one metal atom M and at least one ligand L bonded to the metal atom M.

21 Claims, 26 Drawing Sheets

(51) Int. Cl.

| | | |
|---|---|---|
| *C07F 9/94* | (2006.01) | |
| *H01L 21/02* | (2006.01) | |
| *H01L 51/56* | (2006.01) | |
| *H01L 51/50* | (2006.01) | |
| *H01L 51/05* | (2006.01) | |
| *H01L 51/42* | (2006.01) | |
| *C07C 63/06* | (2006.01) | |
| *C07C 63/68* | (2006.01) | |

(52) U.S. Cl.
CPC .......... *H01L 51/001* (2013.01); *H01L 51/002* (2013.01); *H01L 51/0035* (2013.01); *H01L 51/0077* (2013.01); *H01L 51/0084* (2013.01); *H01L 51/0091* (2013.01); *H01L 51/56* (2013.01); *C07C 63/06* (2013.01); *C07C 63/68* (2013.01); *H01L 51/0558* (2013.01); *H01L 51/4253* (2013.01); *H01L 51/506* (2013.01); *H01L 51/5096* (2013.01)

(56) References Cited

U.S. PATENT DOCUMENTS

| | | | |
|---|---|---|---|
| 5,484,922 | A | 1/1996 | Moore et al. |
| 6,202,591 | B1* | 3/2001 | Witzman .............. C23C 14/243 |
| | | | 118/723 VE |
| 6,326,517 | B1 | 12/2001 | Kume et al. |
| 6,423,429 | B2 | 7/2002 | Kido et al. |
| 6,589,673 | B1 | 7/2003 | Kido et al. |
| 7,632,703 | B2 | 12/2009 | Wu et al. |
| 8,278,652 | B2 | 10/2012 | Krause et al. |
| 8,314,545 | B2 | 11/2012 | Tsuji et al. |
| 9,166,178 | B2 | 10/2015 | Schmid et al. |
| 9,929,362 | B2 | 3/2018 | Maltenberger et al. |
| 10,305,047 | B2* | 5/2019 | Maltenberger .......... C09K 11/06 |
| 2010/0209609 | A1* | 8/2010 | Negishi .................. C23C 14/12 |
| | | | 427/255.6 |
| 2011/0089408 | A1* | 4/2011 | Schmid .................. C07F 1/005 |
| | | | 257/40 |
| 2011/0207043 | A1 | 8/2011 | Yanagawa et al. |
| 2014/0048785 | A1 | 2/2014 | Heuser et al. |
| 2014/0107364 | A1 | 4/2014 | Schmid et al. |
| 2015/0123047 | A1* | 5/2015 | Maltenberger ........ H01L 51/009 |
| | | | 252/519.21 |
| 2016/0181540 | A1 | 6/2016 | Kessler et al. |

FOREIGN PATENT DOCUMENTS

| | | | |
|---|---|---|---|
| DE | 102011007052 | A1 | 10/2012 |
| DE | 102012209523 | A1 | 12/2013 |
| DE | 102013215342 | A1 | 2/2015 |
| EP | 0510541 | B1 | 12/1995 |
| EP | 1220339 | A2 | 7/2002 |
| EP | 1089361 | B1 | 3/2014 |
| JP | H0585060 | B2 | 12/1993 |
| JP | H06172751 | A | 6/1994 |
| JP | 2000191580 | A | 7/2000 |
| JP | 2000191612 | A | 7/2000 |
| JP | 2007146292 | A | 6/2007 |
| JP | 2011173992 | A | 9/2011 |
| JP | 2013505565 | A | 2/2013 |
| WO | 03083169 | A1 | 10/2003 |
| WO | 2008155310 | A1 | 12/2008 |
| WO | 2009034916 | A1 | 3/2009 |
| WO | 2011033023 | A1 | 3/2011 |
| WO | 2012136422 | A | 10/2012 |
| WO | 2013182383 | A1 | 12/2013 |
| WO | 2013182389 | A2 | 12/2013 |

OTHER PUBLICATIONS

Sevryugina, Y. et al., "X-ray Structure and Photoluminescence of Copper(I) 2,6-bis(trifluoromethyl) benzonate," Inorganica Chimica Acta, NL, Elsevier BV, vol. 360, May 10, 2007, 5 pages.

Mayeux, C., et al., "Bonding Between the Cesium Cation and Substituted Benzoic Acids or Benzoate Anions in the Gas Phase: A Density Functional Theory and Mass Spectrometric Study," Collection of Czechoslovak Chemical Communications, vol. 74, Issue 1, Feb. 11, 2009, pp. 167-188.

Legrave, N. et al., "Efficient Preparation of Anhydrous Metallic Triflates and Triflimides under Ultrasonic Activation," European Journal of Organic Chemistry, vol. 2012, No. 5, 2012, 4 pages.

Sevryugina, Y. et al., "Breaking Infinite CuI Carboxylate Helix Held by Cuprophilicity into Discrete Cun Fragments (n=6, 4, 2)," European Journal of Inorganic Chemistry, No. 2, 2008, 11 pages.

Pecqueur, S., "Lewis Acid-Base Theory Applied on Evaluation of New Dopants for Organic Light-Emitting Diodes," Als Dissertation genehmigt, von der Technischen Fakultät der, Friedrich-Alexander-Universität Erlangen-Nürnberg, Jul. 2, 2014, pp. 178.

Schmid, G., et al., "Fluorinated Copper (I) Carboxylates as Advanced Tunable p-Dopants for Organic Light-Emitting Diodes," Advanced Materials, vol. 26, Feb. 12, 2014, pp. 878-885.

Murgatroyd, P.N., "Theory of Space-Charge-Limited Current Enhanced by Frenkel Effect,"Journal of Physics D: Applied Physics, vol. 3, 1979, 6 pages.

Schwoerer, M. et al.,"Organic Molecular Solids" WILEY-VCH, Description, 2007, 1 page.

Steiger, J. et al., "Energetic Trap Distributions in Organic Semiconductors," Synthetic Materials, vol. 129, 2002, 7 pages.

Suzuki, H. et al., "Organobismuth Chemistry," 1st Edition, Elsevier Science, 2001, 3 pages.

* cited by examiner

METHOD FOR PRODUCING AN ORGANIC ELECTRONIC COMPONENT, AND ORGANIC ELECTRONIC COMPONENT

This patent application is a national phase filing under section 371 of PCT/EP2014/079049, filed Dec. 22, 2014, which claims the priority of German patent application 10 2014 114 231.4, filed Sep. 30, 2014, each of which is incorporated herein by reference in its entirety.

TECHNICAL FIELD

The invention relates to a method for producing an organic electronic component wherein the organic electronic layer is obtained by means of gas-phase deposition. The invention further relates to an organic electronic component.

BACKGROUND

Organic electronics is concerned with applications of organic matrix materials for converting light into electrical current and vice versa and with the construction of electrical components using organic semiconductor material. Examples of the former category are for instance photodetectors and organic solar cells, shown diagrammatically in FIG. 1, which convert light into an electrical signal or into electrical current, and organic light-emitting diodes (OLEDs), which are capable of generating light by means of organic electronic materials (see FIG. 2). The second technological field includes, for example, organic field-effect transistors, shown diagrammatically in FIG. 3, in which doping reduces the contact resistance between electrode and semiconductor material, or bipolar transistors.

A feature common to all applications is that they contain electrical transport layers, which have different conduction mechanisms as a function of the composition thereof, as a substantial, functional component. A distinction is generally drawn between an intrinsic p (hole) or n (electron) conductivity of the organic materials. Since charge transport by these organic classes of substances is generally inadequate, they are mixed with additional compounds which are intended to improve the charge transport properties of the layers. This is conventionally achieved by doping with metallic or further organic compounds. One approach to achieving significant improvements in conductivity is that of adding metal complexes.

Inventors of the present invention have accordingly already described the use of bismuth and copper complexes as p-dopants for organic electronic devices, for example, in WO 2013/182389 A2 and WO 2011/033023 A1.

The organic layers of the described devices, which contain a matrix material together with the respective metal complex as p-dopant, were obtained, for example, by means of solvent processes, i.e., wet processing methods. Moreover, organic layers were also produced in the stated patent specifications by means of gas-phase deposition using point sources.

Examples of wet processing methods are in particular printing methods such as inkjet, gravure and offset printing. Spin coating and slot coating are further typical solvent processes.

The production of layers of organic electronic devices by vacuum processes, in contrast, proceeds by means of sublimation, thus by thermal evaporation. The organic layers are here deposited from the gas phase onto a substrate or a pre-existing layer.

The most efficient organic devices are currently produced by the latter process and are now also commercially available from pilot production. The efficiency of the organic electronic devices is also achieved inter alia by the devices being built up from a very large number of individual layers. Each of the layers has a specific physical, electrical function which also relates to its location in the component.

When producing the organic layers by deposition from the gas phase, the matrix material and the doping agent are deposited, for example, by coevaporation, preferably from different sources, onto a substrate or a pre-existing layer.

Point sources are conventionally used for this purpose. For example, the inventors of the present invention carried out a gas-phase deposition of doped organic layers, in each case by means of point sources, in WO 2011/033023 A1 and WO 2013/182389 A2.

When carrying out deposition from point sources, the material to be deposited is evaporated in a crucible under vacuum conditions. Once the material has evaporated, due to the high average free path length under a vacuum ($10^{-5}$ to $10^{-6}$ mbar) the molecules land on the substrate without further collisions. This means that a material needs to be thermally stable only slightly above the sublimation temperature for it to be possible to deposit it undecomposed on the substrate.

Both methods, wet processing methods and deposition from the gas phase via point sources, are comparatively gentle methods. They may therefore be used for numerous different metal complexes.

Although both wet processing methods and gas-phase deposition by means of point sources permit production of organic electronic devices even under industrial conditions, the stated methods are suitable only to a limited extent in particular for coating large-area substrates.

SUMMARY OF THE INVENTION

Embodiments provide a further method for the production of organic electronic components, in particular a method which is also suitable for coating large-area substrates.

In various embodiments a method for producing an organic electronic component is accordingly proposed, wherein the component comprises at least one organic electronic layer. The organic electronic layer here comprises a matrix, wherein the matrix contains a metal complex as dopant. Said dopant may, for example, be a p-dopant. Said metal complex comprises at least one metal atom M and at least one ligand L bound to the metal atom M, wherein the ligands L mutually independently have the following general structure:

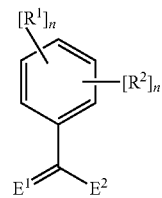

$E^1$ and $E^2$ are here mutually independently oxygen, sulfur, selenium, NH or NR', wherein R' may be selected from the group containing alkyl or aryl and may be attached to the substituted benzene ring of ligand L.

The substituents $R^1$ are mutually independently selected from the group comprising branched or unbranched, fluorinated aliphatic hydrocarbons with 1 to 10 C atoms, wherein n=1 to 5. It is thus, for example, possible for one to five substituents $R^1$ to be present which may in each case mutually independently be selected from the group comprising branched or unbranched, fluorinated aliphatic hydrocarbons with 1 to 10 C atoms. It is thus, for example, possible for a plurality of identical but also a plurality of different substituents $R^1$ to be present.

The substituents $R^2$ are mutually independently selected from the group comprising —CN, branched or unbranched aliphatic hydrocarbons with 1 to 10 C atoms, aryl and heteroaryl, wherein m=0 to at most 5-n. It is thus, for example, possible for one or more substituents $R^2$ to be present which are mutually independently selected from the group comprising —CN, branched or unbranched aliphatic hydrocarbons with 1 to 10 C atoms, aryl and heteroaryl. It is, however, for example, also possible for ligand L to have no substituents $R^2$.

Thus, while ligand L in any event comprises at least one substituent $R^1$, it need not necessarily comprise a substituent $R^2$.

All unsubstituted positions of the benzene ring of ligand L are occupied with hydrogen or deuterium.

The metal M may, for example, be a main group metal or a transition metal.

Deposition of the dopant of the at least one organic electronic layer proceeds by means of a source for gas-phase deposition, wherein the source is configured such that the dopant undergoes collisions with at least one wall of the source.

In contrast with a source as used in the present invention, in a point source the region of the source in which the dopant is evaporated, the outlet orifice of the source and the substrate on which the dopant is deposited are all arranged in a straight line, such that the dopant has direct access to the substrate and collisions with the walls of the source can be avoided.

In a source as used in the method according to the invention, the region of the source in which the dopant is evaporated, the outlet orifice of the source and the substrate are not arranged in a straight line. The source is instead distinguished in that the dopant, once it has been evaporated in a region of the source, still undergoes a deflection within the source before leaving the source and landing on the substrate.

In doing so, the dopant may, for example, undergo collisions with a plurality of walls of the source. For example, the gas stream comprising the dopant may be guided via regions of the source for instance in the form of tubes, wherein the dopant undergoes numerous collisions with walls of the source. The walls of the source may, for example, be heated such that they have a temperature which is at least as high as the sublimation temperature of the dopant.

In comparison with conventional sources for gas-phase deposition, such sources have the advantage of permitting better guidance of the gas stream. This may in particular be advantageous for gas-phase deposition when large-area substrates are to be coated.

In the method according to the invention, the dopant may, for example, undergo several thousand collisions with the walls of the source before leaving the source, but without decomposing.

In many sources, the dopant to be deposited suffers several thousand collisions with the walls of the source before entering the free vacuum via an outlet orifice, for example, in the form of a slot or a plurality of holes. In order to prevent material deposition on the walls of the source, said walls are frequently heated to temperatures of 20-80 Kelvin or even distinctly higher than the actual sublimation point of the dopant to be deposited. The dopant must be capable of withstanding these temperatures during deposition from the gas phase without decomposing.

The inventors of the present invention have established that while conventional metal complexes which are used as dopants in organic layers are indeed sufficiently stable for processing by means of wet processing methods or gas-phase deposition via point sources, they are not sufficiently stable to be deposited by means of sources in which the dopant undergoes collisions with at least one wall of the source.

The inventors of the present method have, for example, observed that while the p-dopants of WO 2013/182389 A2 and WO 2011/033023 A1 may indeed generally be deposited together with suitable matrix materials in the form of organic layers by means of solvent processes and by gas-phase deposition from point sources, many of the compounds stated therein are not sufficiently thermally stable for deposition by means of sources in which the dopant undergoes collisions with walls of the source. The inventors of the present invention have, for example, recognized that metal complexes, for example, of copper or bismuth, are not sufficiently stable for deposition if they do not comprise substituents of the form $R^1$. For example, benzoic acid derivatives with a fluorinated benzene ring but without substituents in the form of $R^1$ are not sufficiently stable to be used in the method according to the invention.

The inventors of the present invention have recognized that metal complexes as used in the method according to the invention according to claim 1 surprisingly have sufficient thermal stability to be evaporated and deposited by means of a source, wherein the source is configured such that the dopant undergoes collisions with at least one wall of the source.

The inventors have, for instance, in particular established that, by introducing at least one substituent $R^1$ which is a branched or unbranched, fluorinated aliphatic hydrocarbon with 1 to 10 C atoms, it is possible to achieve a distinct improvement in the thermal stability of the entire complex, whereby deposition via sources according to claim 1 is enabled for the first time.

At the same time, the metal complexes as used in the method according to the invention are distinguished not only by elevated temperature stability but simultaneously by sufficiently good doping strengths.

Layers of organic electronic devices which are produced with the method according to the invention are additionally distinguished by elevated optical transparency in the visible range.

The metal complexes used in the method according to the invention are obtainable at prices comparable to those for conventional metal complexes and may additionally be produced without major technical effort.

Using sources in which the dopant undergoes collisions with at least one wall of the source overall allows organic electronic components to be manufactured in a less complex, more cost-effective and time-saving manner. The method according to the invention is therefore particularly well suited to use on an industrial scale. The method according to the invention is in particular distinctly better suited to coating large-area substrates than conventional methods which make use, for example, of point sources. The method according to the invention is thus a large-area coating method.

Some terms are briefly defined below:

For the purposes of the present invention the term "organic electronic component" means and/or comprises in particular organic transistors, organic light-emitting diodes, light-emitting electrochemical cells, organic solar cells, photodiodes and organic photovoltaics in general.

For the purposes of the present invention, the term "p-dopant" comprises or means in particular materials which exhibit Lewis acidity and/or are capable of forming complexes with the matrix material in which these materials (albeit only formally) act as a Lewis acid.

A series of preferred embodiments of the method according to the invention are explained below:

According to one particularly preferred embodiment, the method according to the invention makes use of a linear source in gas-phase deposition.

In linear sources deposition proceeds from the gas phase via a slot as outlet orifice, for instance in the form of a row of holes. The molecule here often suffers several thousand collisions with the walls of the source before finally entering the free vacuum through the slot or plurality of holes. In order to prevent material deposition on the walls of the linear source, said walls are often heated to temperatures of 20-80 Kelvin above the actual sublimation point. Heating to still higher temperatures is also possible.

Conventional dopants usually decompose in the event of collisions with the walls of the source. The inventors have, for example, recognized that although many of the metal complexes of WO 2013/182389 A2 and WO 2011/033023 A1 are indeed sufficiently stable for deposition by means of point sources, it is not possible, as is experimentally demonstrated, to deposit them by means of linear sources in which the complexes are exposed to collisions with the walls of the source.

The compounds described in the article by Schmid et al. "Fluorinated Copper(I) Carboxylates as Advanced Tunable p-Dopants for Organic Light-Emitting Diodes" (Advanced Materials 2014, vol. 26, 6, 878-885) are also p-doping agents. While the inventors of the present invention were able to evaporate and characterize the compounds described therein undecomposed in a point source, transfer to a linear source was however not possible.

According to a preferred embodiment, the method according to the invention uses a metal complex of the described form which is Lewis acidic, i.e., which acts as an electron pair acceptor. This has proved to be particularly preferred for interaction with the matrix materials.

One embodiment of the invention relates to the method according to the invention, wherein the metal complex comprises a plurality of identical ligands L. Such complexes are usually simpler to produce than metal complexes with ligands L of different kinds.

One embodiment of the invention relates to the method according to the invention, wherein the metal complex comprises at least two ligands L of different kinds. Such complexes may also be deposited in sources which are configured such that the dopant collides with at least one wall of the source.

One embodiment of the invention relates to the method according to the invention, wherein, in addition to ligand L, the metal complex comprises still further ligands of another formula which differs from L. Such complexes are also characterized by elevated thermal stability.

According to another further development of the invention, the method according to the invention uses a metal complex which comprises at least one open or partially accessible coordination site. This has likewise proved to be particularly preferred for interaction with the matrix materials.

One preferred embodiment of the invention relates to the method according to the invention, wherein the metal M of the metal complex is selected from the group of main group metals and transition metals. In particular, the metal M may be the main group metals of groups 13 to 15 of the periodic table of elements and the metals Cu, Cr, Mo, Rh and Ru.

These complexes have proved to be effective p-dopants in organic layers of organic electronic devices. Good p-doping agent effects are achieved with the complexes of said metals thanks to the Lewis acidity thereof. The described metal complexes are moreover easy to produce and do not require any complex production methods. In addition, the conductivity of organic layers may moreover be adapted to particular requirements simply via the concentration of said metals in the doping agents.

Another further development of the invention relates to the method according to the invention, wherein the metal M of the metal complex is bismuth or copper. For example, it may be a metal complex with bismuth in oxidation states III or V. Particular preference is here given to bismuth complexes in oxidation state III. The metal complex may, for example, be a copper(I) or copper(II) complex. Particular preference is here given to copper complexes in oxidation state I.

Metal complexes of copper and bismuth have proved to be particularly effective p-doping agents which are simple to produce. Organic electronic devices comprising hole-transport layers comprising said doping agents are, for example, distinguished by particularly good conductivity. In addition, corresponding complexes are particularly thermally stable.

In one particularly preferred embodiment, the substituent $R^1$ is an at least difluorinated substituent, i.e., $R^1$ comprises at least two fluorine atoms. It is still more preferred for the substituent $R^1$ to be a perfluorinated substituent. The higher the degree of fluorination, the stronger the stabilizing effect of the substituent on the metal complex.

One particularly preferred embodiment of the present invention relates to the method according to the invention, wherein at least one of the substituents $R^1$ of ligand L in the metal complex is a —$CF_3$ group.

The inventors of the present invention have recognized that the method according to the invention with this kind of metal complexes is particularly to be preferred since such metal complexes have particularly high thermal stability and therefore do not decompose even when used in sources in which the metal complex collides with at least one wall of the source.

The inventors have observed that the electronic and steric properties of the —$CF_3$ group as substituent $R^1$ of ligand L result in particularly stable metal complexes. In particular, very high levels of thermal stability are ensured, such that metal complexes with the —$CF_3$ group as substituent $R^1$ of ligand L only decompose at temperatures far above the sublimation point.

The —$CF_3$ group also promotes a higher Lewis acidity of the metal complex and leads to particularly good doping agent strengths, which promotes conductivity in the organic layer of the produced organic electronic component.

In addition, in comparison with other fluorinated aliphatic hydrocarbons, ligands with —$CF_3$ substituents are more widespread in starting materials for the production of ligand L, such that ligands in which the substituent $R^1$ is a —$CF_3$ group are frequently more readily available and more inexpensive than ligands with other substituents $R^1$.

Another embodiment of the invention relates to the method according to the invention, wherein ligand L comprises precisely two substituents $R^1$, which each form a —$CF_3$ group.

The inventors of the present invention have recognized that, surprisingly, a further improvement in the thermal stability of the metal complex may be achieved by using two —$CF_3$ groups in contrast with using, for example, only one —$CF_3$ group. This results in particularly good results on application of the organic layer comprising said metal complex as doping agent by means of sources in which the doping agent, i.e., the dopant, undergoes collisions with at least one of the walls of the sources.

Another embodiment of the invention relates to the method according to the invention, wherein ligand L comprises precisely two substituents $R^1$, which each form a —$CF_3$ group and are arranged in 3,5-position on the benzene ring of ligand L.

The inventors of the present invention have recognized that complexes comprising ligand L with said connectivity permit particularly high thermal stability. The inventors have established that particularly good stabilization of the metal complex is possible thanks to the steric bulk of the groups located in 3,5-position on the benzene ring.

Another embodiment of the invention accordingly relates to the method according to the invention, wherein the substituents $R^2$ are mutually independently selected from the group comprising —CN, methyl, ethyl, n-propyl, iso-propyl, n-butyl, iso-butyl, tert-butyl and substituted or unsubstituted phenyl.

The inventors of the present invention have recognized that it is possible to evaporate such complexes by means of sources in which the dopant undergoes collisions with at least one of the walls of the source without decomposition of the complex. Complexes comprising ligand L in which not all the substituents are fluorinated hydrocarbons may thus also be used in linear sources.

Another embodiment of the invention relates to the method according to the invention, in which ligand L of the metal complex comprises no substituents $R^2$, i.e., m=0.

Since unfluorinated hydrocarbon substituents have higher reactivity than fluorinated hydrocarbon substituents, dispensing with a substituent $R^2$ leads to a further improvement in stability and thus better depositability from the gas phase by means of sources in which the metal complex collides with at least one of the walls of the source.

In another preferred further development of the invention, the metal complex comprises precisely two substituents $R^1$ or still more substituents $R^1$. Two or more substituents $R^1$ lead to particularly good outward shielding of the complex and therefore permit particularly good stabilization of the metal complex.

Another further development of the invention relates to the method according to the invention, wherein both $E^1$ and $E^2$ of ligand L of the metal complex are oxygen. In this case, ligand L is a benzoate derivative substituted with fluorinated hydrocarbons.

The inventors of the present invention have established that such metal complexes are particularly well suited to the production of organic electronic devices by means of deposition via sources, in which the dopant undergoes collisions with at least one of the walls of the source, since they are easy to produce, yield metal complexes with good doping agent strengths and meet particularly high requirements for thermal stability. In particular, benzoic acid derivatives are often readily commercially obtainable or may be produced without major technical effort.

One particularly preferred embodiment of the invention relates to the method according to the invention, wherein ligand L of the metal complex is mutually independently selected from the group comprising:

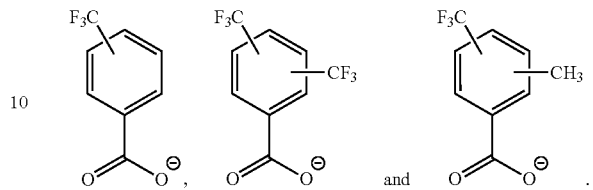

If a plurality of ligands L are present, all ligands L of the metal complex may be mutually independently selected. For example, a plurality of different ones of the stated ligands L may be present in the metal complex or all ligands L may also be identical.

The inventors of the present invention have established that metal complexes comprising ligands L from this group have particularly good thermal stability and additionally have particularly good doping agent properties. It has surprisingly been found that these metal complexes are particularly suitable for deposition by means of sources in which the metal complexes undergo collisions with at least one wall of the source and nevertheless do not decompose in the source.

A further preferred embodiment of the invention relates to the method according to the invention, wherein ligand L of the metal complex is mutually independently selected from the group comprising:

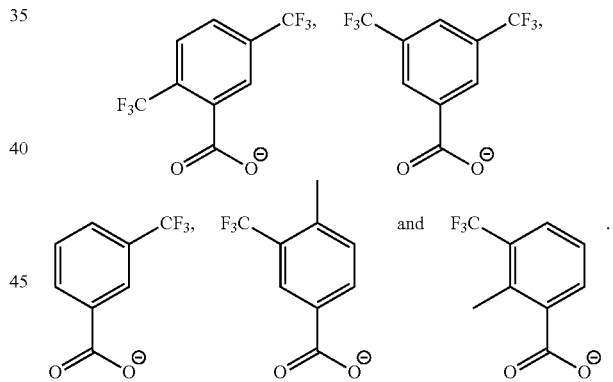

The stated examples of ligand L are commercially available at reasonable prices and therefore need not be produced in-house. They are therefore also particularly suitable for applications on an industrial scale.

A still more preferred embodiment of the invention relates to the method according to the invention, wherein ligand L of the metal complex is

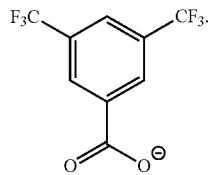

Using a derivative of benzoic acid comprising two —CF$_3$ substituents in 3,5-position results in metal complexes which are still thermally stable far above the sublimation temperature. These complexes are particularly well suited to a method involving deposition via sources in which collisions occur with at least one of the walls of the sources, for example, linear sources. They additionally give rise to organic electronic devices with excellent electrical properties.

In another embodiment of the method according to the invention, the metal complex used is a mononuclear metal complex, i.e., a metal complex with only one central atom.

In an embodiment of the method according to the invention which differs therefrom, polynuclear metal complexes are used. In this manner, it is frequently possible to adjust the conductivity of the organic layers to be deposited still more effectively thanks to the availability of a plurality of Lewis acidic centers.

A further development of the invention relates to the method according to the invention in which only homoleptic metal complexes are used. Such complexes are often less complex to produce since they only comprise one kind of ligand of the formula of ligand L. Also, as a consequence, no other ligands which might potentially reduce the stability of the entire complex are introduced.

Another embodiment of the invention relates to the method according to the invention, wherein ligand L is mutually independently attached to the metal atom M of the metal complex by one of the following forms of coordination:

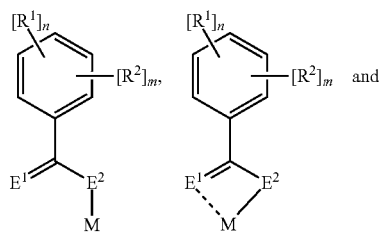

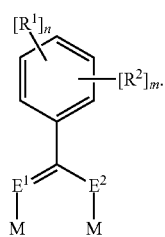

Experimental findings by the inventors show that the bond to the metal atom M may take many and varied forms. The ligands may be attached in monodentate, bidentate or bridging manner in order to bring about the increase in temperature stability.

One particularly preferred embodiment of the invention relates to the method according to the invention, wherein the metal complex is a bismuth complex and wherein ligand L may mutually independently have the following general structure:

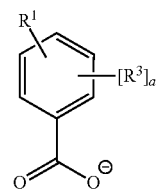

wherein substituent $R^1$ is selected from the group comprising branched or unbranched, fluorinated aliphatic hydrocarbons with 1 to 10 C atoms, and
wherein substituent $R^3$ is selected from the group comprising branched or unbranched fluorinated or unfluorinated aliphatic hydrocarbons with 1 to 10 C atoms, aryl and heteroaryl, wherein a may be equal to 0 or 1.

The inventors of the present invention have recognized that bismuth complexes with said ligands have particularly high thermal stability. Said complexes may therefore be particularly effectively deposited by means of sources in which collisions occur with at least one of the walls of the source, for which reason the method permits production of organic electronic components with particularly little technical effort and is thus particularly inexpensive.

Another embodiment of the invention relates to the method according to the invention, wherein the metal complex has a decomposition temperature which is greater than 10 Kelvin, furthermore greater than 20 Kelvin and in particular over 40 Kelvin above the sublimation temperature of the metal complex. The decomposition temperature is most preferably over 70 Kelvin above the sublimation temperature of the metal complex.

The higher is the decomposition temperature above the sublimation temperature of the metal complex, the more stable are the metal complexes to collisions with the walls of the source.

Another embodiment of the invention relates to the method according to the invention, wherein the matrix material of the organic electronic layer, which is deposited together with the metal complex, for example, by means of coevaporation, is selected from the group comprising or consisting of one or more of the following materials, which may, for example, be used in hole-transport layers:

NPB (N,N'-bis(naphthalen-1-yl)-N,N'-bis(phenyl)benzidine),
β-NPB (N,N'-bis(naphthalen-2-yl)-N,N'-bis(phenyl)benzidine)
TPD (N,N'-bis(3-methylphenyl)-N,N'-bis(phenyl)benzidine)
spiro-TPD (N,N'-bis(3-methylphenyl)-N,N'-bis(phenyl)benzidine)
spiro-NPB (N,N'-bis(naphthalen-1-yl)-N,N'-bis(phenyl) spiro)
DMFL-TPD N,N'-bis(3-methylphenyl)-N,N'-bis(phenyl)-9,9-dimethylfluorene)
N,N-bis(naphthalen-1-yl)-N,N'-bis(phenyl)-2,2-dimethylbenzidine
N,N'-bis(3-methylphenyl)-N,N'-bis(phenyl)-9,9-spirofluorene
N,N'-bis(naphthalen-1-yl)-N,N'-bis(phenyl)-9,9-spirofluorene
DMFL-NPB (N,N-bis(naphthalen-1-yl)-N,N-bis(phenyl)-9,9-dimethylfluorene)
DPFL-TPD (N,N'-bis(3-methylphenyl)-N,N'-bis(phenyl)-9,9-diphenylfluorene)

DPFL-NPB (N,N-bis(naphthalen-1-yl)-N,N'-bis(phenyl)-9,9-diphenylfluorene)
spiro-TAD (2,2',7,7'-tetrakis(N,N-diphenylamino)-9,9'-spirobifluorene)
9,9-bis[4-(N,N-bis-biphenyl-4-yl-amino)phenyl]-9H-fluorene
9,9-bis[4-(N,N-bis-naphthalen-2-yl-amino)phenyl]-9H-fluorene
9,9-bis[4-(N,N'-bis-naphthalen-2-yl-N,N'-bis-phenylamino)phenyl]-9H-fluorene
N,N'-bis(phenanthren-9-yl)-N,N'-bis(phenyl)benzidine
2,7-bis[N,N-bis(9,9-spiro-bifluoren-2-yeamino]-9,9-spirobifluorene
2,2'-bis[N,N-bis(biphenyl-4-yeamino]-9,9-spiro-bifluorene
2,2'-bis(N,N-di-phenylamino)-9,9-spiro-bifluorene
di-[4-(N,N-ditolylamino)phenyl]cyclohexane
2,2',7,7'-tetra(N,N-ditolyl)amino-spiro-bifluorene
N,N,N',N'-tetra-naphthalen-2-yl-benzidine
2,2',7,7'-tetrakis[(N-naphthalenyl(phenyeamino]-9,9-spirobifluorene
spiro-TTB (2,2',7,7'-tetrakis-(N,N'-di-p-methylphenylamino)-9,9'-spirobifluorene)
titanium oxide phthalocyanine
copper phthalocyanine
2,3,5,6-tetrafluoro-7,7,8,8,-tetracyano-quinodimethane
4,4',4''-tris(N-3-methylphenyl-N-phenylamino)triphenylamine
4,4',4''-tris(N-(2-naphthyl)-N-phenylamino)triphenylamine
4,4',4''-tris(N-(1-naphthyl)-N-phenylamino)triphenylamine
4,4',4''-tris(N,N-diphenylamino)triphenylamine
pyrazino[2,3-f][1,10]phenanthroline-2,3-dicarbonitrile
N,N,N',N'-tetrakis(4-methoxyphenyl)benzidine.

These materials have proved effective as matrix materials in organic electronic components.

Another embodiment of the invention relates to the method according to the invention, wherein the at least one organic electronic layer of the organic electronic device to be produced by the method is an electron-blocking layer. Coevaporation here proceeds by means of sources, wherein collisions occur with at least one wall of the source, for example, with linear sources, using at least partially electron-conducting matrix materials.

Typical electron-conducting materials are here:
2,2',2''-(1,3,5-benzenetriyl)tris(1-phenyl-1H-benzimidazole)
2-(4-biphenylyl)-5-(4-tert.-butylphenyl)-1,3,4-oxadiazole
2,9-dimethyl-4,7-diphenyl-1,10-phenanthroline
8-hydroxyquinolinolato-lithium
4-(naphthalen-1-yl)-3,5-diphenyl-4H-1,2,4-triazole
1,3-bis[2-(2,2'-bipyridin-6-yl)-1,3,4-oxadiazo-5-yl]benzene
4,7-diphenyl-1,10-phenanthroline
3-(4-biphenylyl)-4-phenyl-5-tert.-butylphenyl-1,2,4-triazole
bis(2-methyl-8-quinolinolate)-4-(phenylphenolato) aluminum
6,6'-bis[5-(biphenyl-4-yl)-1,3,4-oxadiazo-2-yl]-2,2'-bipyridyl
2-phenyl-9,10-di(naphthalen-2-yl)anthracene
2,7-bis[2-(2,2'-bipyridin-6-yl)-1,3,4-oxadiazo-5-yl]-9,9-dimethylfluorene
1,3-bis[2-(4-tert-butylphenyl)-1,3,4-oxadiazo-5-yl]benzene
2-(naphthalen-2-yl)-4,7-diphenyl-1,10-phenanthroline
2,9-bis(naphthalen-2-yl)-4,7-diphenyl-1,10-phenanthroline
tris(2,4,6-trimethyl-3-(pyridin-3-yl)phenyl)borane
1-methyl-2-(4-(naphthalen-2-yl)phenyl)-1H-imidazo[4,5-f][1,10]phenanthroline.

Blocking and limiting electron flow is of great significance, for example, for highly efficient organic light-emitting diodes (OLEDs) and the method according to the invention is therefore highly beneficial for the purposes of industrial manufacture.

In addition to providing the method according to the invention, the invention also relates to an organic electronic component comprising at least one organic electronic layer. The organic electronic layer comprises a matrix, wherein the matrix contains a bismuth complex as dopant, for example, as p-dopant. The bismuth complex comprises at least one ligand L attached to the bismuth atom, wherein the ligands L may mutually independently have the following general structure:

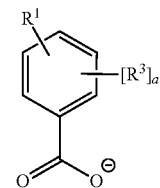

wherein the one substituent $R^1$ is selected from the group comprising branched or unbranched, fluorinated aliphatic hydrocarbons with 1 to 10 C atoms, and
wherein the one substituent $R^3$ is selected from the group comprising branched or unbranched fluorinated or unfluorinated aliphatic hydrocarbons with 1 to 10 C atoms, aryl and heteroaryl, wherein a may be equal to 0 or 1.

The inventors of the present invention have established that organic electronic devices of this form may be manufactured with distinctly less technical effort than conventional organic electronic devices.

This is possible because devices according to the invention comprise bismuth complexes of the form just described which are distinguished by particularly high thermal stability. It is therefore also possible to use manufacturing methods which require higher thermal stability of the metal complexes, thus a manufacturing method in which, in the gas deposition source, complexes collide with at least one wall of the source or with one another. Manufacture may, for example, be carried out by means of linear sources which require particularly high thermal stability.

A further embodiment of the organic electronic component according to the invention is distinguished in that ligand L is independently selected from the group comprising:

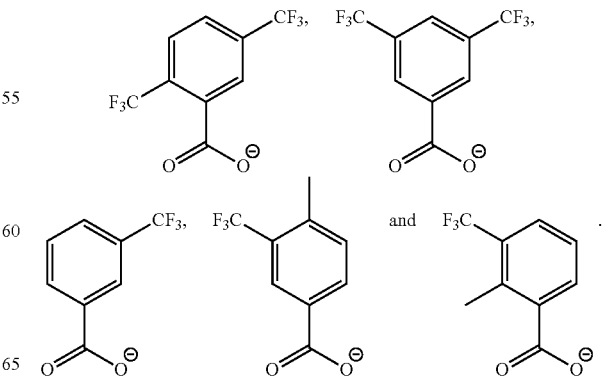

Apart from being particularly simple to manufacture, these components are also particularly inexpensive thanks to the thermal stability of the bismuth complexes, since the stated ligands are commercially available at reasonable prices and thus in-house manufacture is not necessary.

One particularly preferred embodiment of the organic electronic component according to the invention relates to a component, wherein ligand L of the bismuth complex is substituted in positions 3 and 5 of the benzene ring. Such complexes are particularly stable.

One particularly preferred embodiment of the organic electronic component according to the invention relates to a component, wherein ligand L of the bismuth complex is

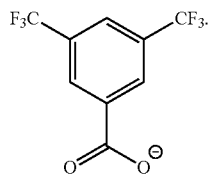

One particularly preferred embodiment of the organic electronic component according to the invention relates to a component, wherein the bismuth complex is the complex

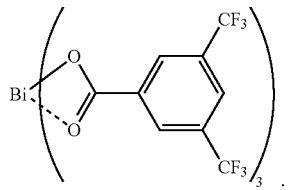

The inventors of the present invention have observed that this complex exhibits both good doping agent properties and particularly high temperature stability. The complex is still stable at temperatures 70° C. above its sublimation temperature and therefore excellently well suited to manufacturing methods which demand high thermal stability of the doping agents used. The complex is also excellently well suited to gas-phase deposition in sources which demand particular stability of the complex, in particular sources in which collisions occur with at least one wall of the source. The complex may, for example, be applied with little effort together with the matrix material in the context of deposition by means of linear sources.

For these reasons, organic electronic devices comprising the stated complex are also particularly simple and inexpensive to produce on a large industrial scale and at the same time have organic electronic layers with very good electrical properties, for example, with regard to conductivity.

The above-stated components together with the claimed components described in the exemplary embodiments for use according to the invention are not subject to any particular exceptional conditions with regard to size, shape, material selection and technical design and therefore the selection criteria known in the field of use may be applied without restriction.

BRIEF DESCRIPTION OF THE DRAWINGS

Further details, features and advantages of the subject matter of the invention may be inferred from the following description of the figures and the associated examples and reference examples.

In the figures.

DETAILED DESCRIPTION OF ILLUSTRATIVE EMBODIMENTS

Figure 1:
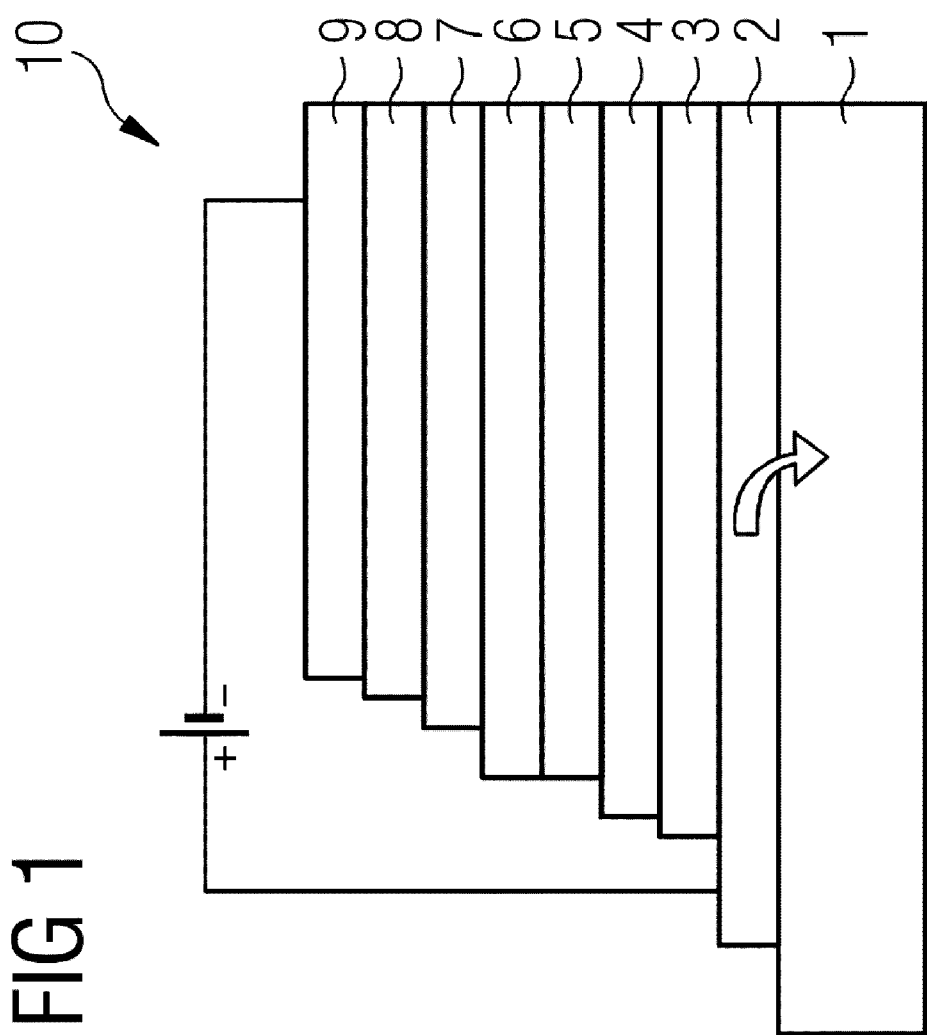
FIG. 1 is a schematic diagram of the structure of an organic light-emitting diode.
Figure 2:
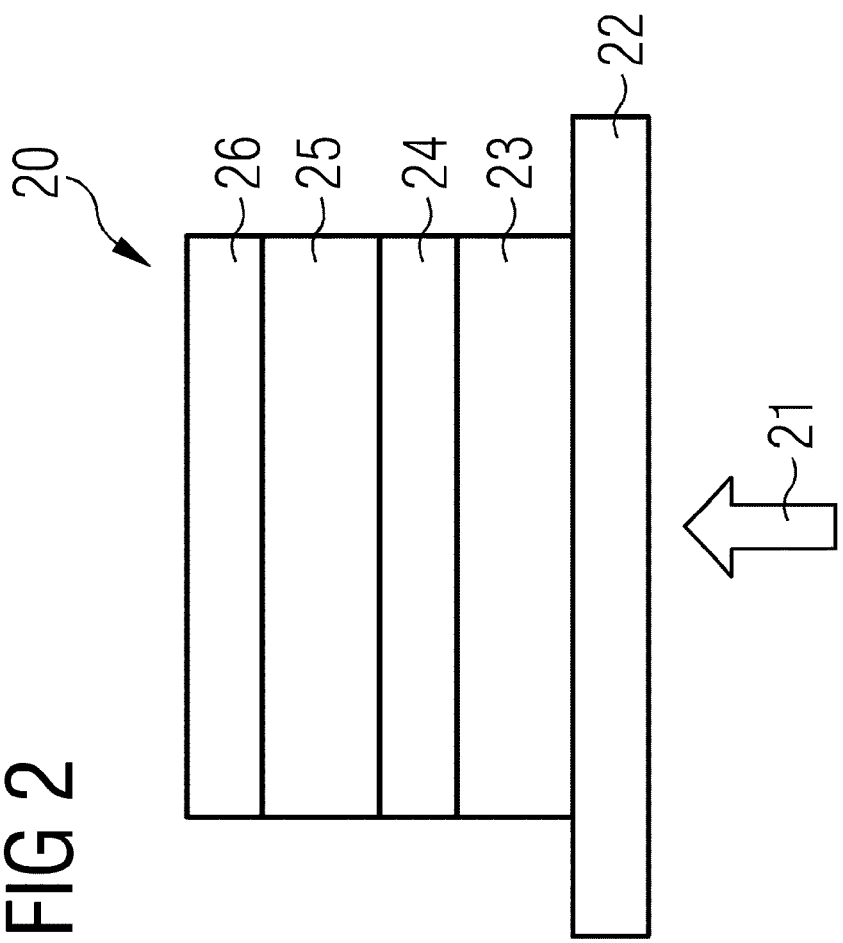
FIG. 2 is a schematic diagram of the structure of an organic solar cell.
Figure 3:
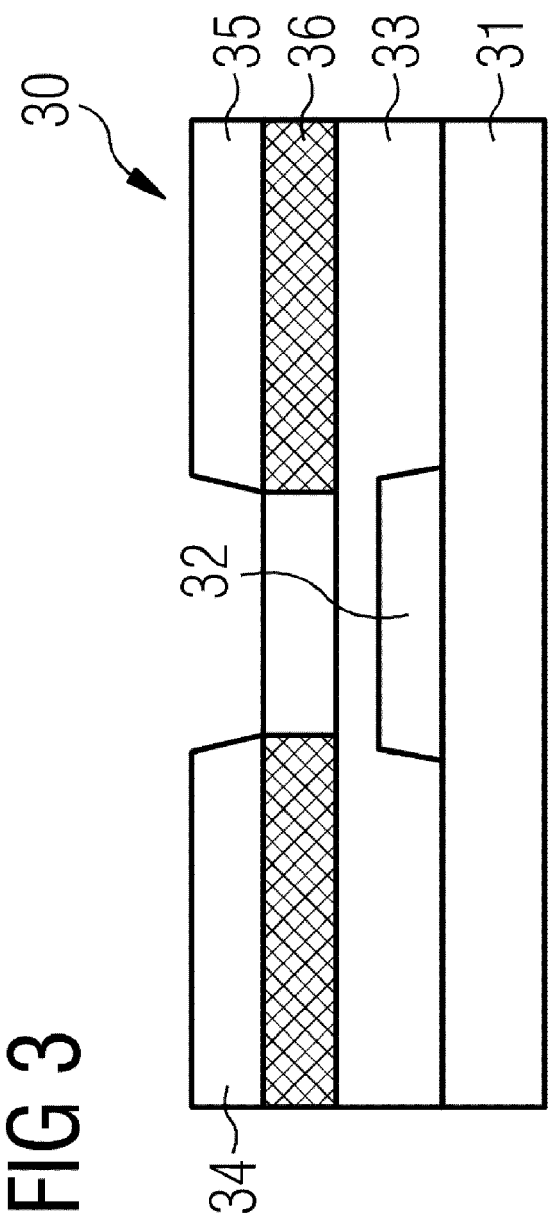
FIG. 3 is a schematic diagram of a possible cross-section of an organic field-effect transistor.

FIG. 1 is a schematic diagram of the structure of an organic light-emitting diode (10). The light-emitting diode is made up of a glass layer (1); Transparent Conductive Oxide (TCO) or PEDOT:PPS or PANT layer (2); hole-injection layer (3); hole-transport layer (HTL) (4); emitter layer (EML) (5); hole-blocking layer (HBL) (6); electron-transport layer (ETL) (7); electron-injection layer (8) and a cathode layer (9);

FIG. 2 is a schematic diagram of the structure of an organic solar cell with PIN structure (20) which converts light (21) into electrical current. The solar cell consists of a layer of indium-tin oxide (22); a p-doped layer (23); an absorption layer (24); an n-doped layer (25) and a metal layer (26);

FIG. 3 is a schematic diagram of a possible cross-section of an organic field-effect transistor (30). A gate electrode (32), a gate dielectric (33), a source and drain contact (34+35) and an organic semiconductor (36) are applied onto a substrate (31). The crosshatched portions indicate the portions where contact doping is helpful.

Figure 4:
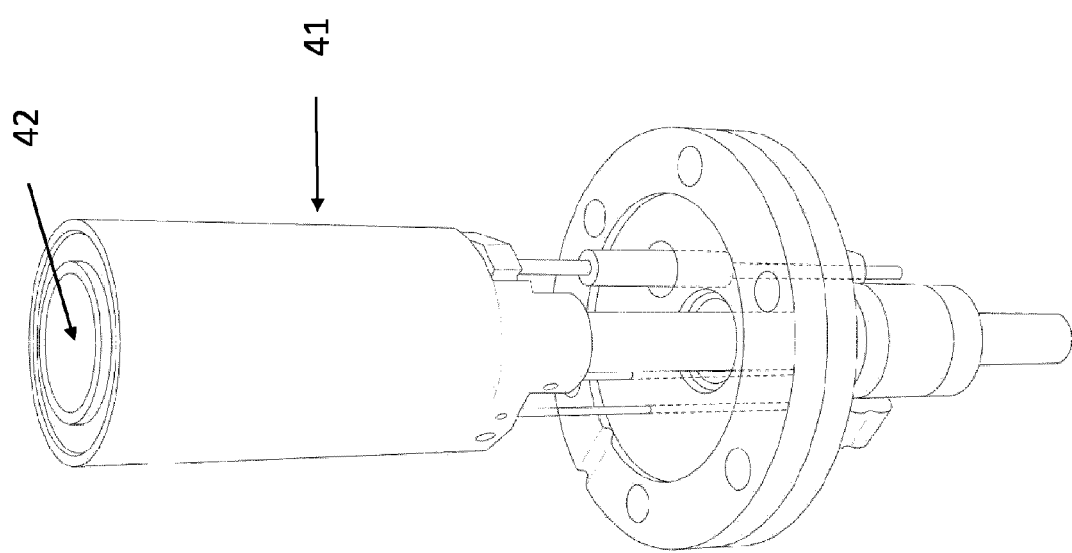
FIG. 4 shows the structure of a prior art point source.

FIG. 4 shows the structure of a prior art point source from Creaphys. The point source has a crucible (41). The material to be deposited is evaporated in the crucible under vacuum conditions. Once the material has evaporated, the molecules leave the point source via the outlet orifice (42). Because of the large average free path length under a vacuum ($10^{-5}$ to $10^{-6}$ mbar), the molecules, for example, of a metal complex acting as dopant, land without further collisions on the substrate. This means that a material needs to be thermally stable only slightly above the sublimation temperature for it to be possible to deposit it undecomposed on the substrate. In particular, a doping agent deposited by means of a point source does not land on walls of the source, but, by being directly arranged at the orifice of the source, may instead be deposited directly on the substrate to be coated. The region of the crucible, in which the dopant evaporates, together with the outlet orifice and the substrate are thus in a rectilinear arrangement. In particular, the dopant can be deposited without being deflected via line systems or spraying systems before it lands on the substrate.

Figure 5:
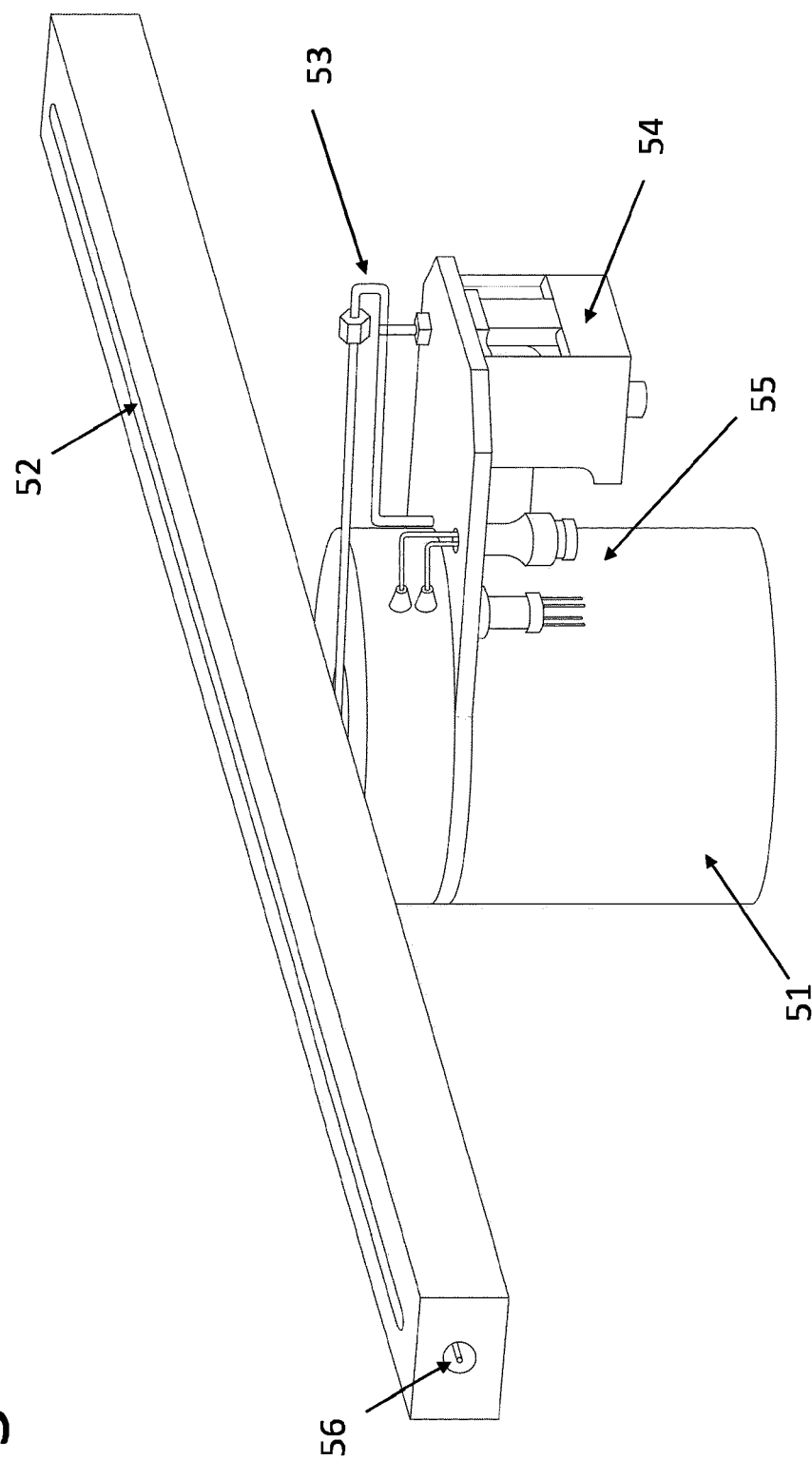
FIG. 5 shows the structure of a linear source, taking a schematic diagram of a linear source.

FIG. 5 shows the structure of a linear source, taking a schematic diagram of a linear source from Vecco by way of example. The linear source has a crucible (51), which may be removable. Once the material to be deposited, for example, the dopant, has evaporated in the crucible, the dopant, which is in the gas phase, is guided via lines (53) to the outlet orifice (52). The outlet orifice (52) may here, for example, take the form of a slot or consist of a row of holes. The linear source does not provide the dopant with direct, rectilinear access to the substrate, the dopant instead being often repeatedly deflected in the linear source. The dopant consequently collides numerous times with the walls of the linear source. The linear source may furthermore contain controllable valves (54), flow controllers (56) and corresponding cabling (55) for electronic control for instance of the heating device or the valves. Purposeful guidance of the gas stream means that large-area deposition can be achieved particularly effectively.

Figure 6:
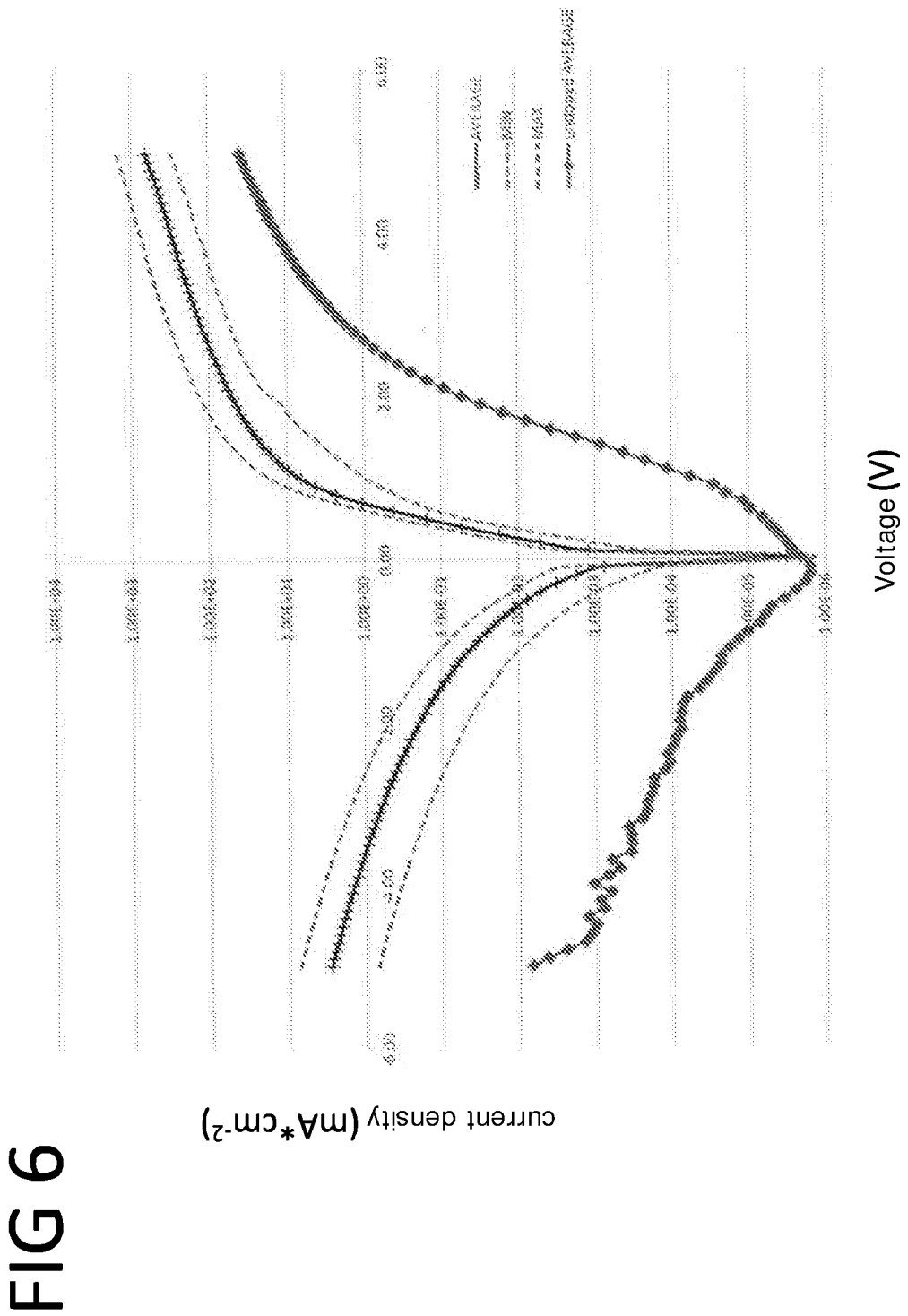
FIG. 6 shows, with regard to example I, current density plotted against voltage for the undoped matrix material and for the doped matrix material.

FIG. 6 shows, for example, I current density plotted against voltage for the undoped matrix material and for the doped matrix material. The matrix material used was the hole conductor 2,2',7,7'-tetra(N,N-ditolyl)amino-9,9-spirobifluorene, abbreviated to spiro-TTB. The current density-voltage characteristic curve demonstrates the adequate doping behavior of 15% Cu(3,5-tfmb) in the hole conductor spiro-TTB.

Figure 7:
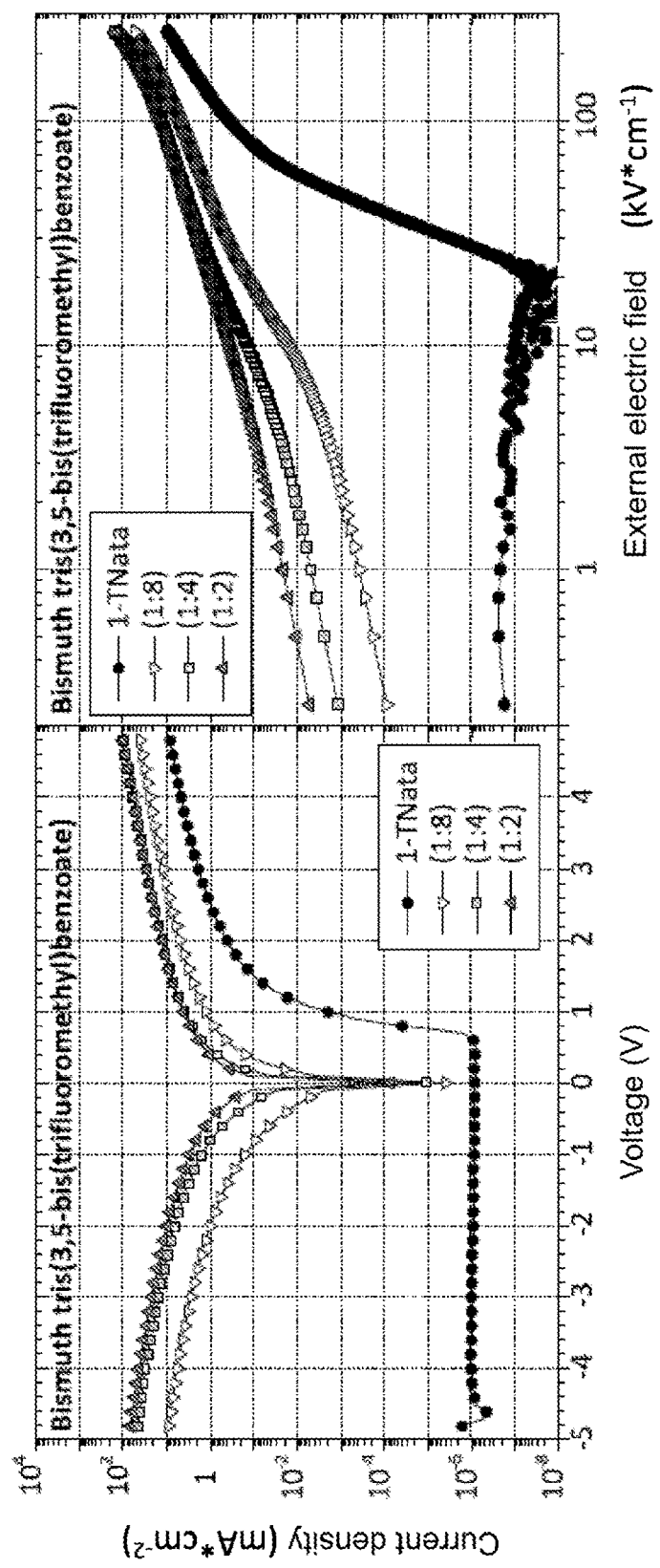
FIG. 7 shows, with regard to example II, current density plotted against voltage and current density plotted against external field strength for 1-TNata doped with bismuth(III) tris-3,5-trifluoromethylbenzoate.

FIG. 7 shows with regard to example II current density plotted against voltage and current density plotted against external field strength for 1-TNata doped with bismuth(III) tris-3,5-trifluoromethylbenzoate. The measurements were made on doped matrix materials produced by means of point sources in order to permit a comparison of electrical properties under identical conditions with the comparative examples. Measurement was made at each of three different doping agent contents. The voltage characteristic curve demonstrates good conductivities and substantiates the good doping agent strength of bismuth(III) tris-3,5-trifluoromethylbenzoate.

Figure 8:
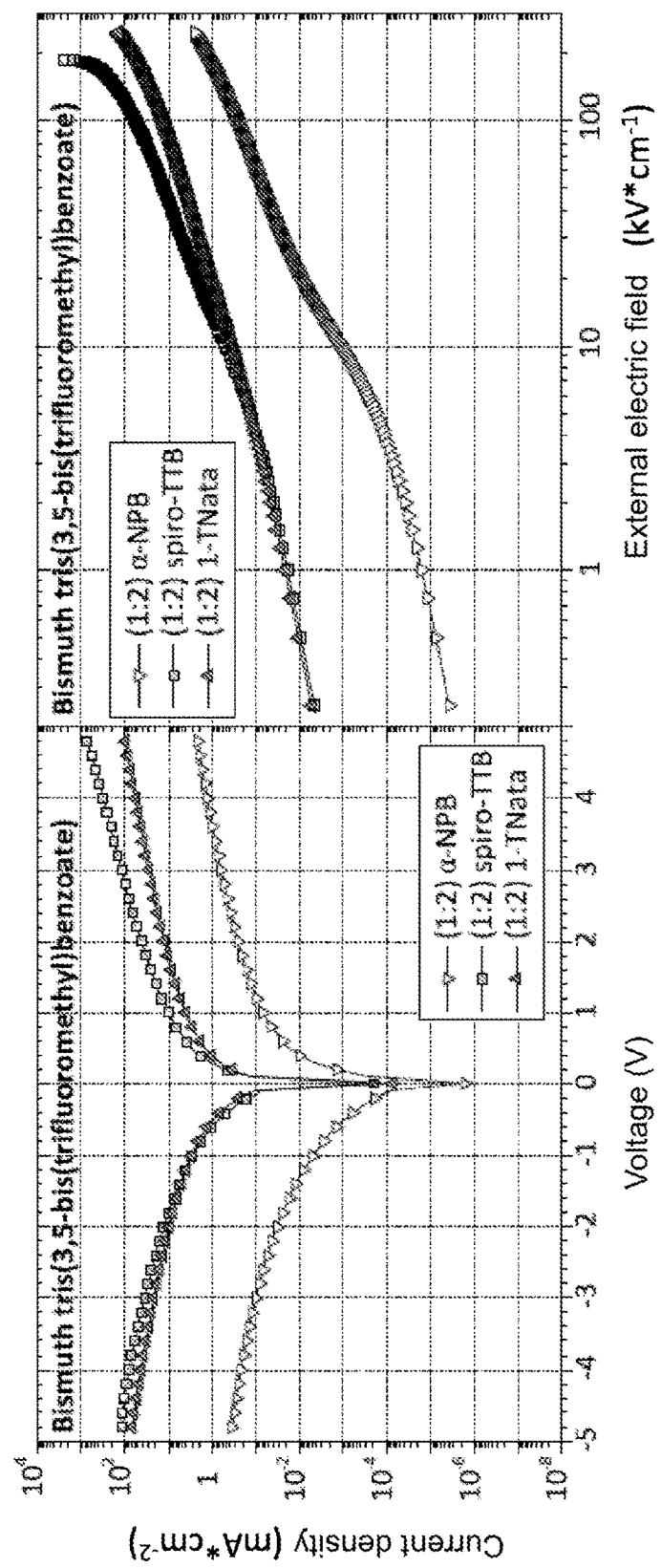
FIG. 8 shows, with regard to example II, current density plotted against voltage and current density plotted against external field strength for the matrix materials 1-TNata, spiro-TTB and α-NPB doped with bismuth(III) tris-3,5-trifluoromethylbenzoate.

FIG. 8 shows with regard to example II current density plotted against voltage and current density plotted against external field strength for the matrix materials 1-TNata, spiro-TTB and α-NPB doped with bismuth(III) tris-3,5-trifluoromethylbenzoate.

Figure 9:
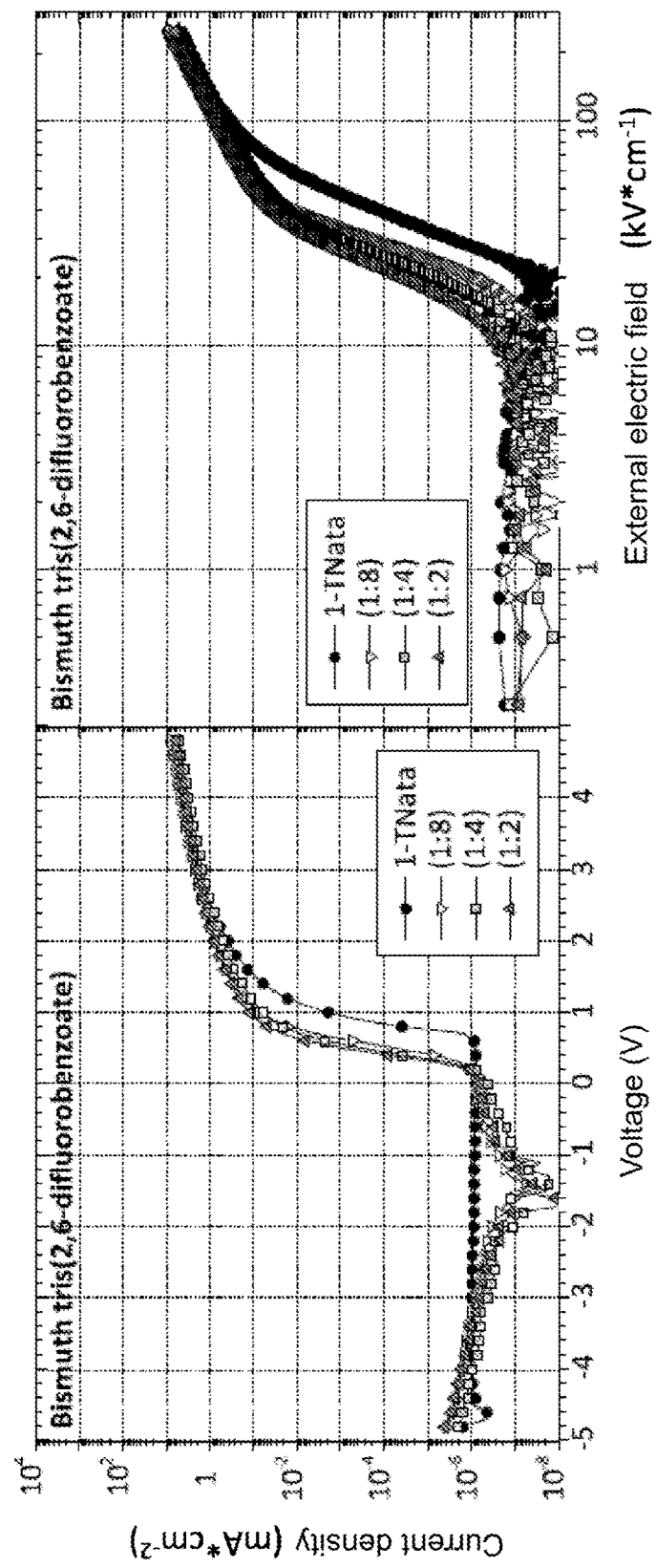
FIG. 9 shows, with regard to reference example I, current density plotted against voltage and current density plotted against external field strength for 1-TNata doped with bismuth(III) tris(2,6-difluorobenzoate) for the doped matrix material obtained by deposition by means of point sources.

FIG. 9 shows with regard to reference example I current density plotted against voltage and current density plotted against external field strength for 1-TNata doped with bismuth(III) tris(2,6-difluorobenzoate) for the doped matrix material obtained by deposition by means of point sources. Measurement was made at each of three different doping agent contents.

Figure 10:
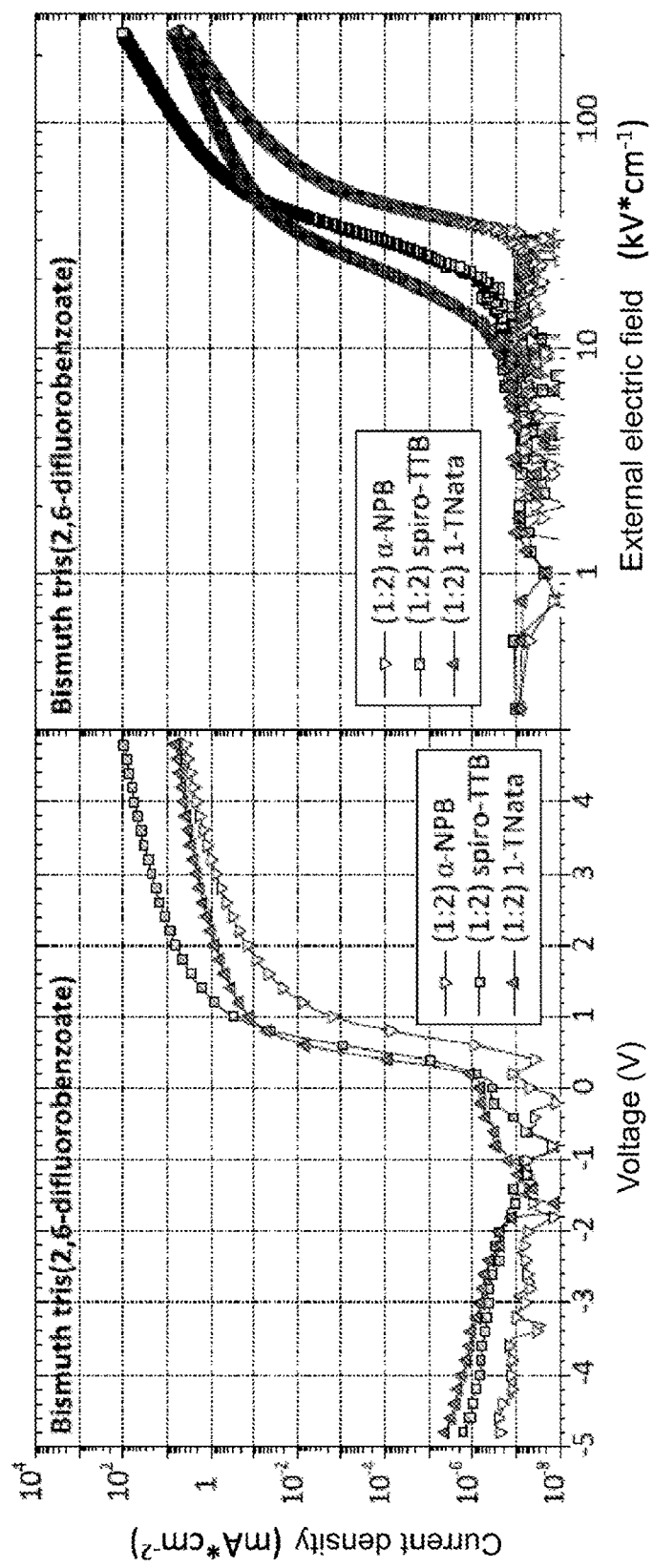
FIG. 10 shows, with regard to reference example I, current density plotted against voltage and current density plotted against external field strength for the matrix materials 1-TNata, spiro-TTB and α-NPB doped with bismuth (III) tris(2,6-difluorobenzoate)

FIG. 10 shows with regard to reference example I current density plotted against voltage and current density plotted against external field strength for the matrix materials 1-TNata, spiro-TTB and α-NPB doped with bismuth(III) tris(2,6-difluorobenzoate).

Figure 11:
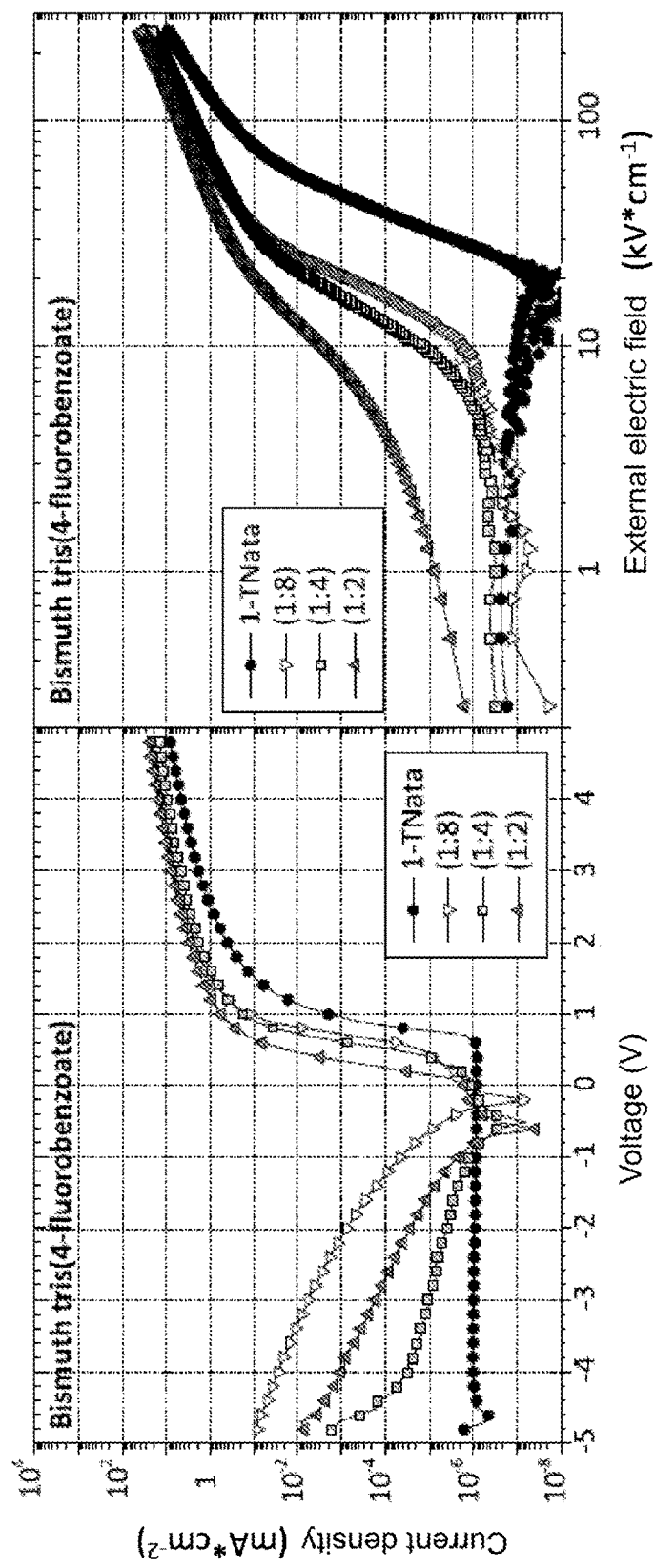
FIG. 11 shows, with regard to reference example II, current density plotted against voltage and current density plotted against external field strength for 1-TNata doped with bismuth(III) tris(4-fluorobenzoate) for the doped matrix material obtained by deposition by means of point sources.

FIG. 11 shows with regard to reference example II current density plotted against voltage and current density plotted against external field strength for 1-TNata doped with bismuth(III) tris(4-fluorobenzoate) for the doped matrix material obtained by deposition by means of point sources. Measurement was made at each of three different doping agent contents.

Figure 12:
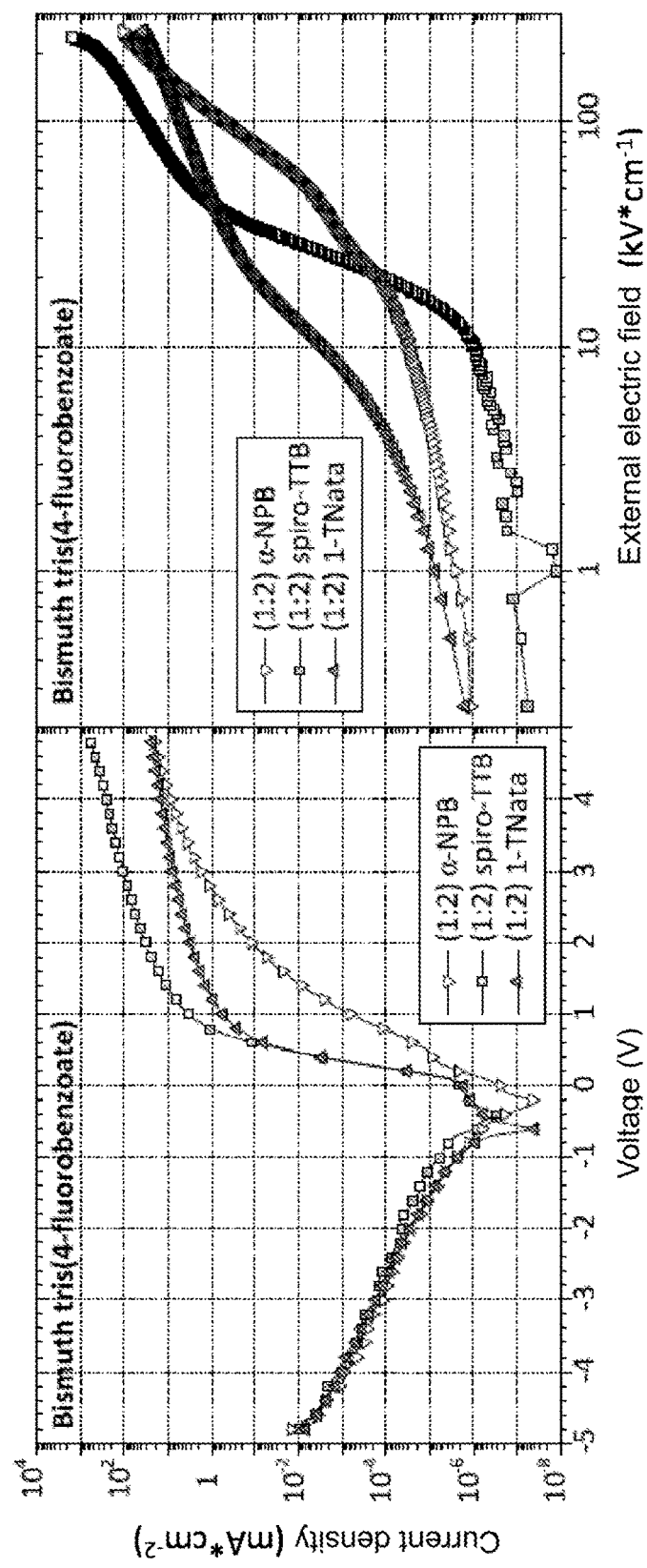
FIG. 12 shows, with regard to reference example II, current density plotted against voltage and current density plotted against external field strength for the matrix materials 1-TNata, spiro-TTB and α-NPB doped with bismuth (III) tris(4-fluorobenzoate)

FIG. 12 shows with regard to reference example II current density plotted against voltage and current density plotted against external field strength for the matrix materials 1-TNata, spiro-TTB and α-NPB doped with bismuth(III) tris(4-fluorobenzoate).

Figure 13:
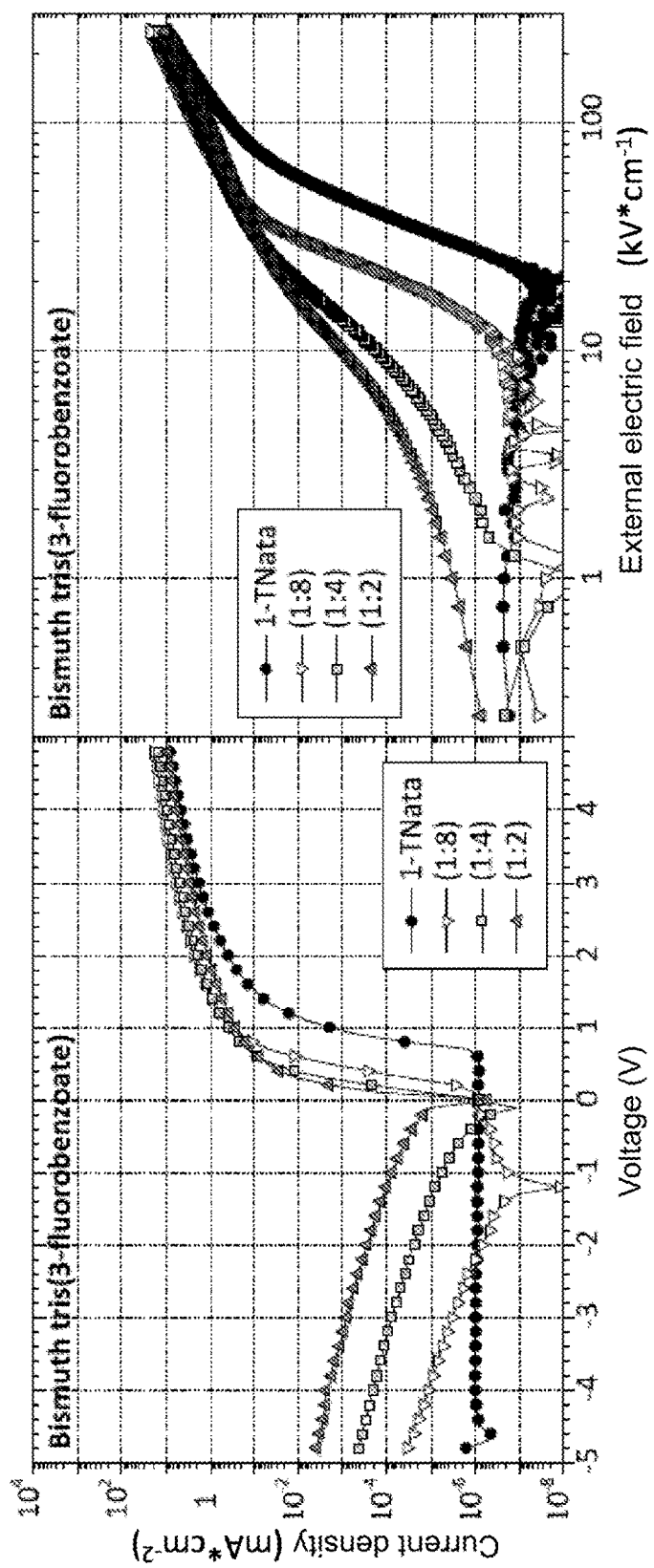
FIG. 13 shows, with regard to reference example III, current density plotted against voltage and current density plotted against external field strength for 1-TNata doped with bismuth(III) tris(3-fluorobenzoate) for the doped matrix material obtained by deposition by means of point sources.

FIG. 13 shows with regard to reference example III current density plotted against voltage and current density plotted against external field strength for 1-TNata doped with bismuth(III) tris(3-fluorobenzoate) for the doped matrix material obtained by deposition by means of point sources. Measurement was made at each of three different doping agent contents.

Figure 14:
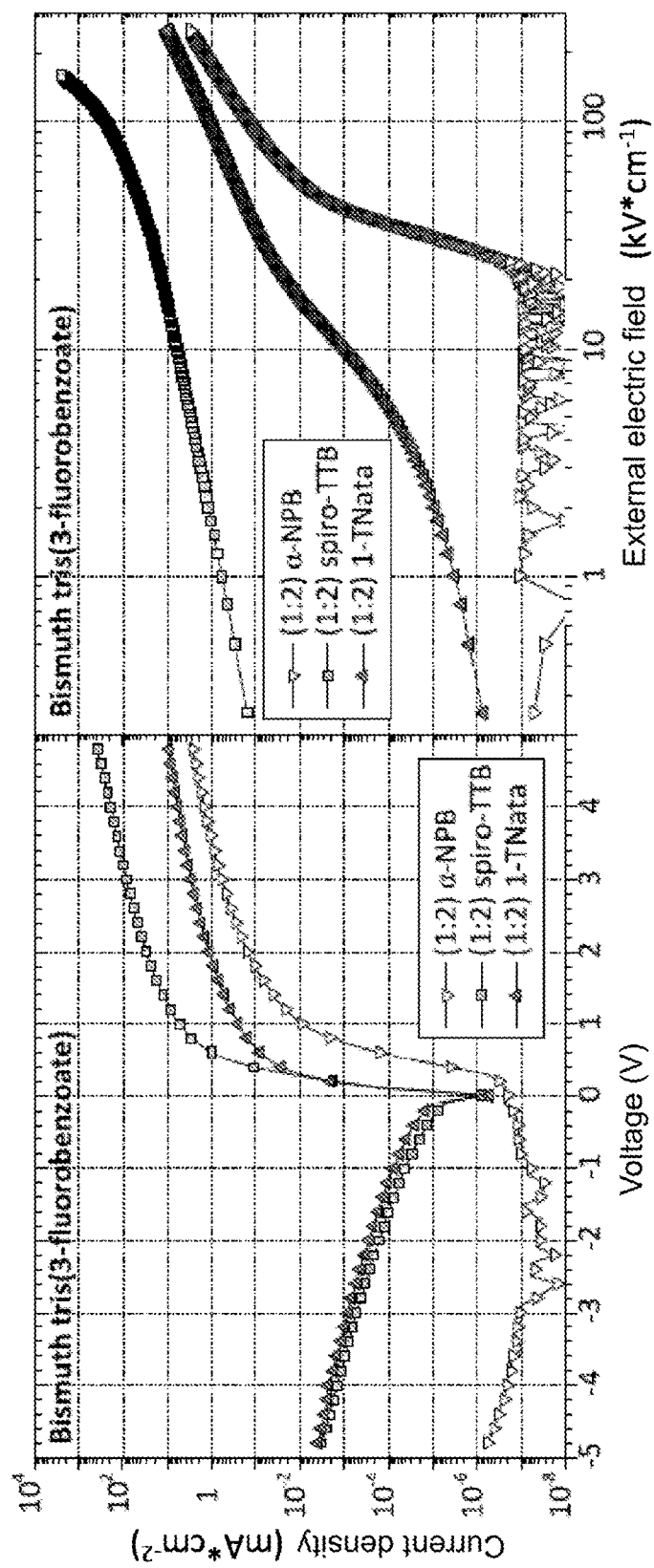
FIG. 14 shows, with regard to reference example III, current density plotted against voltage and current density plotted against external field strength for the matrix materials 1-TNata, spiro-TTB and α-NPB doped with bismuth (III) tris(3-fluorobenzoate)

FIG. 14 shows with regard to reference example III current density plotted against voltage and current density plotted against external field strength for the matrix materials 1-TNata, spiro-TTB and α-NPB doped with bismuth (III) tris(3-fluorobenzoate).

Figure 15:
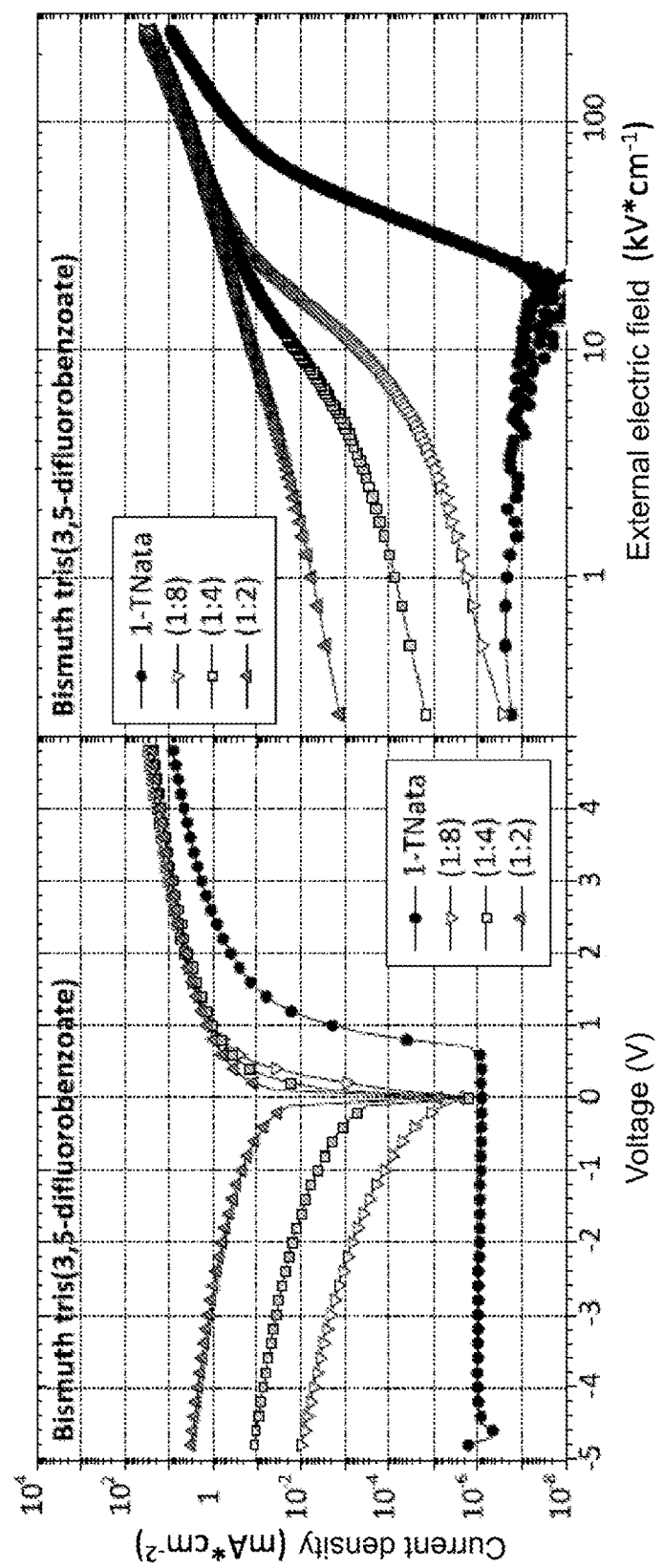
FIG. 15 shows, with regard to reference example IV, current density plotted against voltage and current density plotted against external field strength for 1-TNata doped with bismuth(III) tris(3,5-difluorobenzoate) for the doped matrix material obtained by deposition by means of point sources.

FIG. 15 shows with regard to reference example IV current density plotted against voltage and current density plotted against external field strength for 1-TNata doped with bismuth(III) tris(3,5-difluorobenzoate) for the doped matrix material obtained by deposition by means of point sources. Measurement was made at each of three different doping agent contents.

Figure 16:
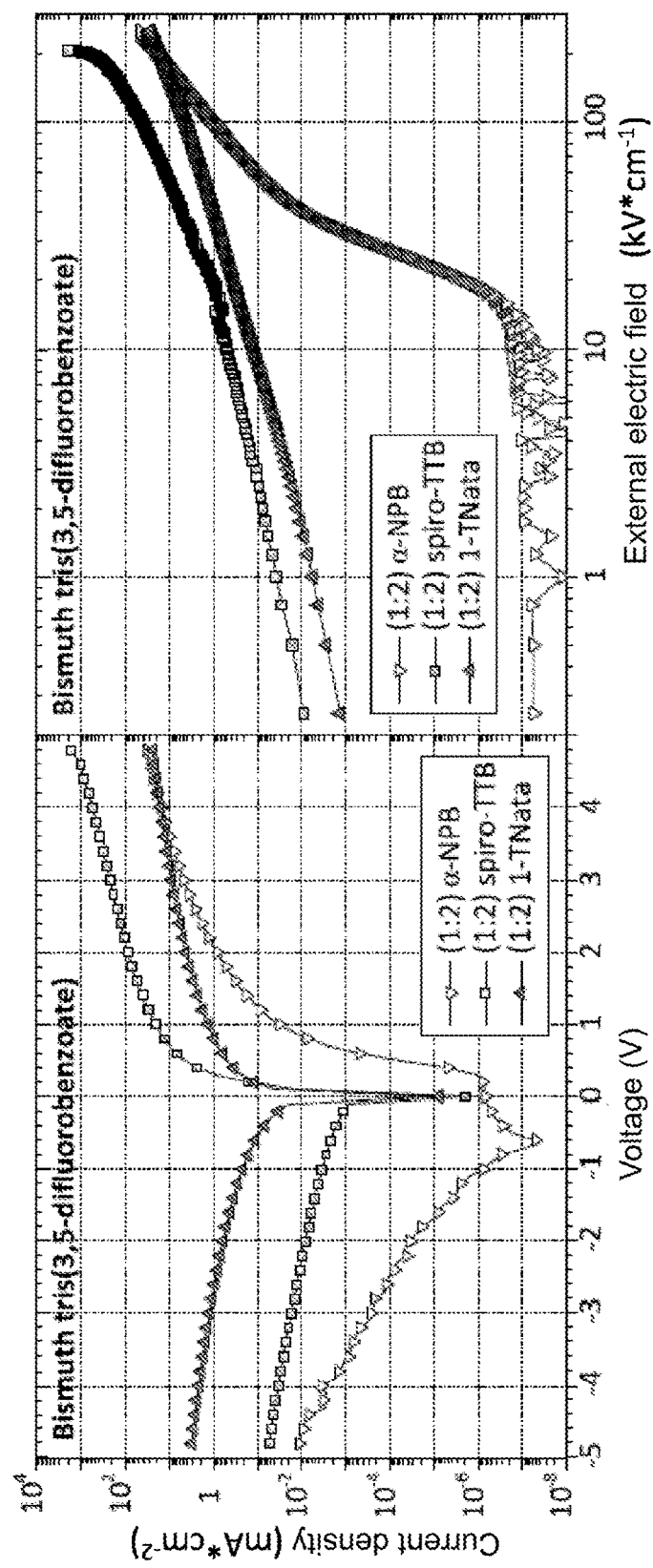
FIG. 16 shows, with regard to reference example IV, current density plotted against voltage and current density plotted against external field strength for the matrix materials 1-TNata, spiro-TTB and α-NPB doped with bismuth (III) tris(3,5-difluorobenzoate)

FIG. 16 shows with regard to reference example IV current density plotted against voltage and current density plotted against external field strength for the matrix materials 1-TNata, spiro-TTB and α-NPB doped with bismuth (III) tris(3,5-difluorobenzoate).

Figure 17:
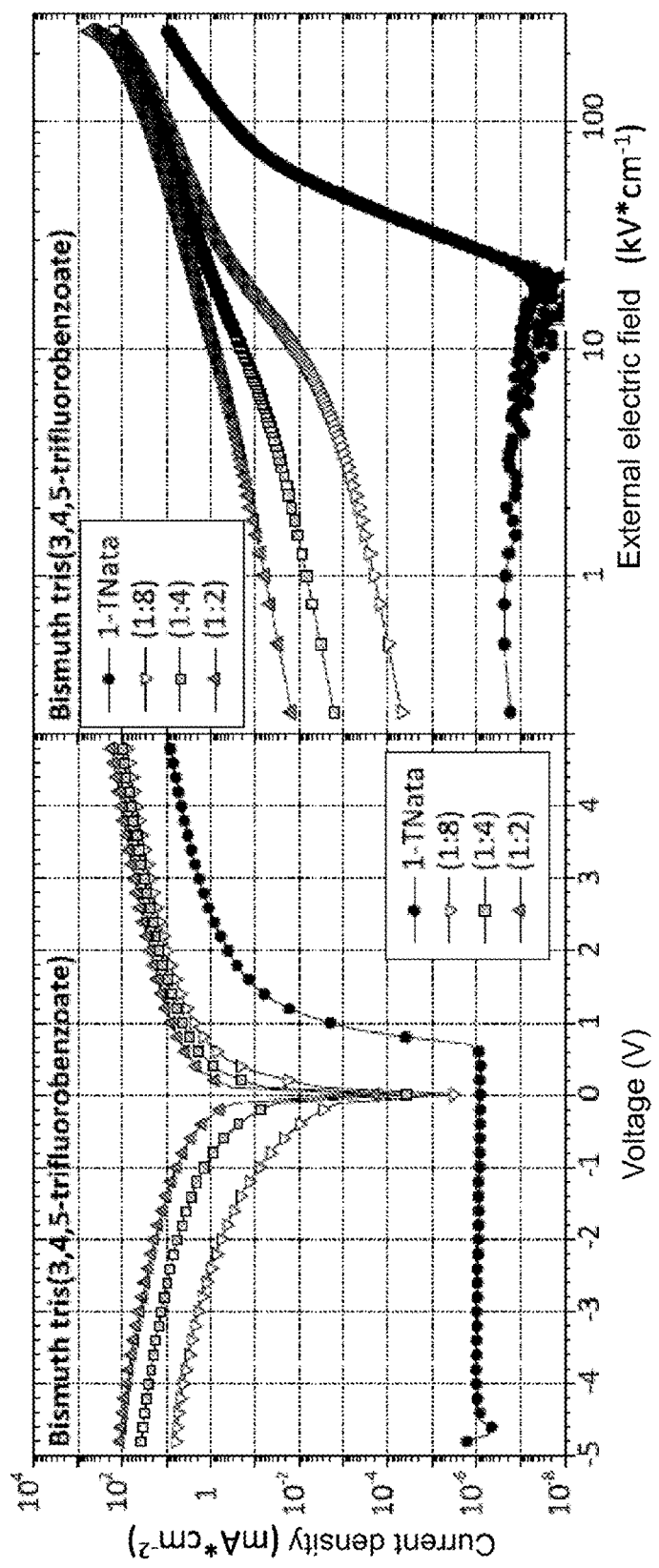
FIG. 17 shows, with regard to reference example V, current density plotted against voltage and current density plotted against external field strength for 1-TNata doped with bismuth(III) tris(3,4,5-trifluorobenzoate) for the doped matrix material obtained by deposition by means of point sources.

FIG. 17 shows with regard to reference example V current density plotted against voltage and current density plotted against external field strength for 1-TNata doped with bismuth(III) tris(3,4,5-trifluorobenzoate) for the doped matrix material obtained by deposition by means of point sources. Measurement was made at each of three different doping agent contents.

Figure 18:
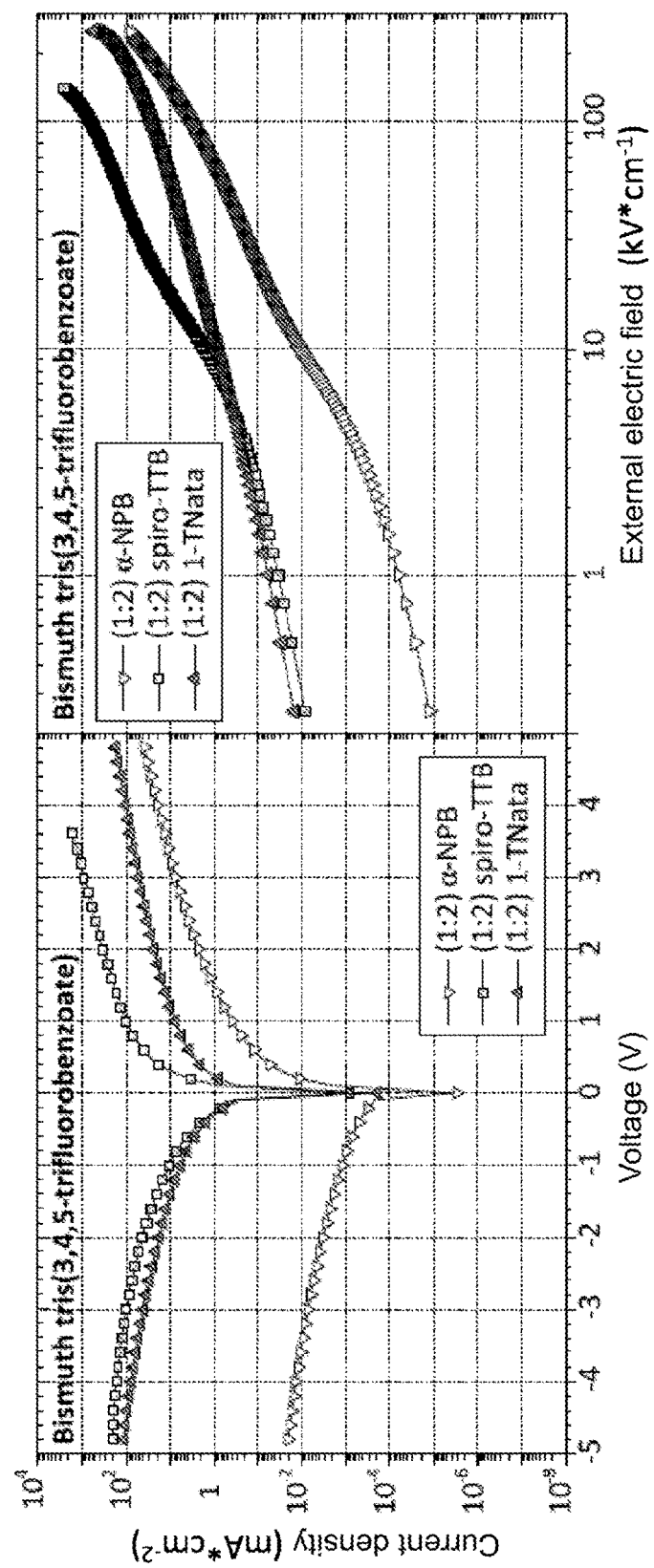
FIG. 18 shows, with regard to reference example V, current density plotted against voltage and current density plotted against external field strength for the matrix materials 1-TNata, spiro-TTB and α-NPB doped with bismuth (III) tris(3,4,5-trifluorobenzoate)

FIG. 18 shows with regard to reference example V current density plotted against voltage and current density plotted against external field strength for the matrix materials 1-TNata, spiro-TTB and α-NPB doped with bismuth(III) tris(3,4,5-trifluorobenzoate).

Figure 19:
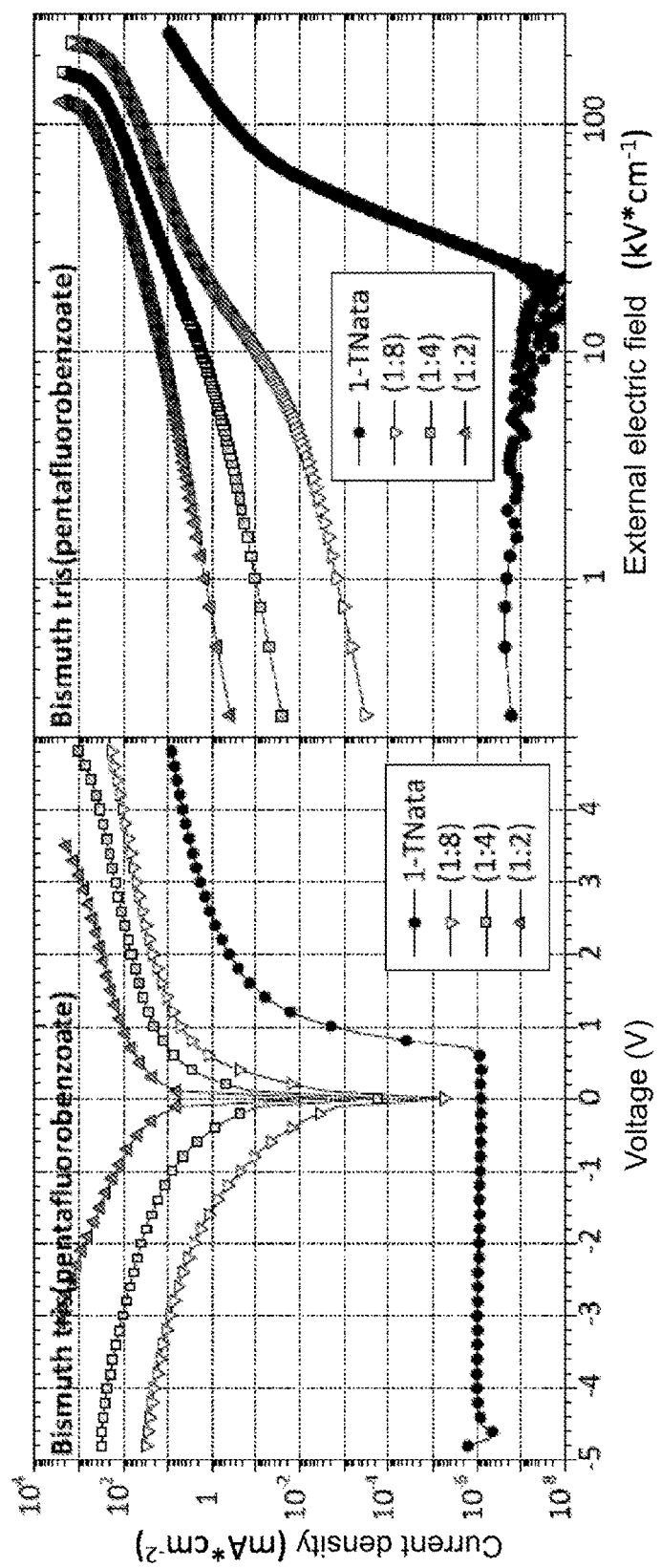
FIG. 19 shows, with regard to reference example VI, current density plotted against voltage and current density plotted against external field strength for 1-TNata doped with bismuth(III) tris(perfluorobenzoate) for the doped matrix material obtained by deposition by means of point sources.

FIG. 19 shows with regard to reference example VI current density plotted against voltage and current density plotted against external field strength for 1-TNata doped with bismuth(III) tris(perfluorobenzoate) for the doped matrix material obtained by deposition by means of point sources. Measurement was made at each of three different doping agent contents.

Figure 20:
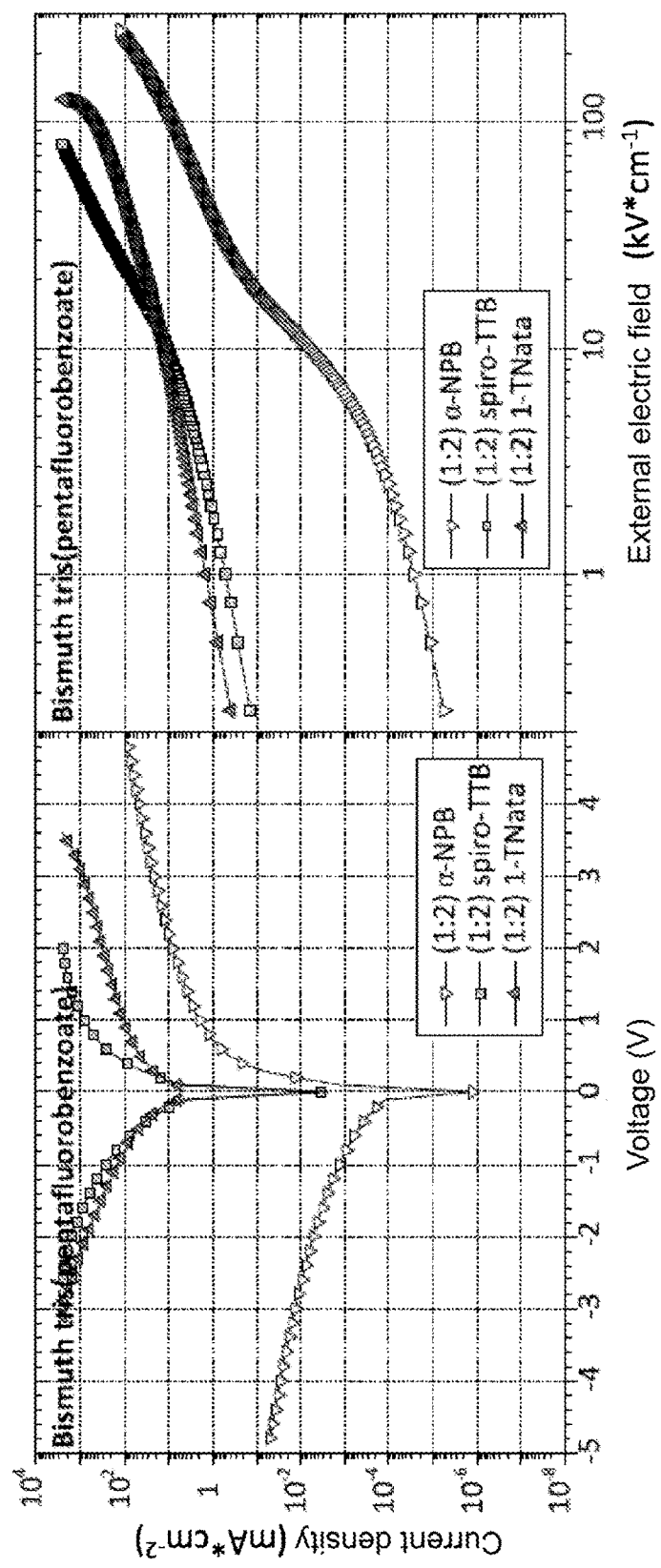
FIG. 20 shows, with regard to reference example VI, current density plotted against voltage and current density plotted against external field strength for the matrix materials 1-TNata, spiro-TTB and α-NPB doped with bismuth (III) tris(perfluorobenzoate)

FIG. 20 shows with regard to reference example VI current density plotted against voltage and current density plotted against external field strength for the matrix materials 1-TNata, spiro-TTB and α-NPB doped with bismuth (III) tris(perfluorobenzoate).

Figure 21:
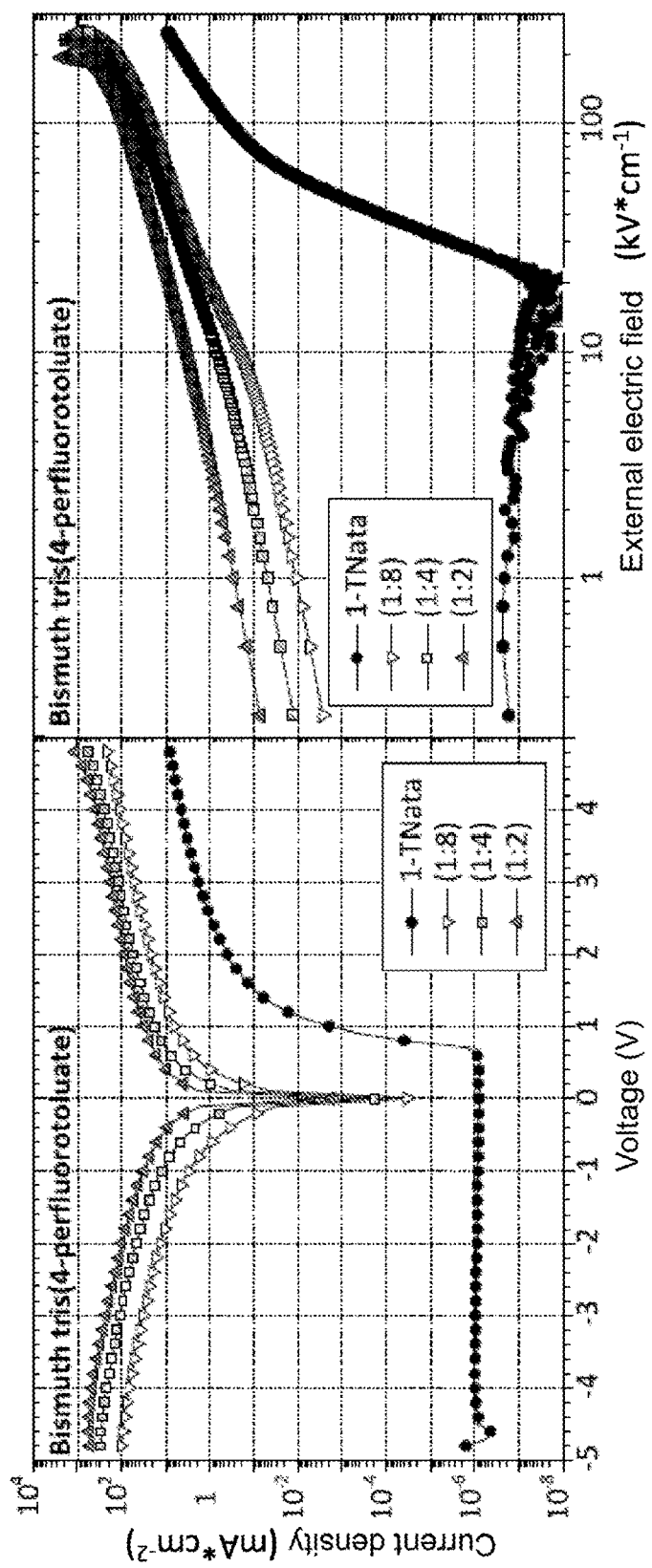
FIG. 21 shows, with regard to reference example VII, current density plotted against voltage and current density plotted against external field strength for 1-TNata doped with bismuth(III) tris(4-perfluorotoluate) for the doped matrix material obtained by deposition by means of point sources.

FIG. 21 shows with regard to reference example VII current density plotted against voltage and current density plotted against external field strength for 1-TNata doped with bismuth(III) tris(4-perfluorotoluate) for the doped matrix material obtained by deposition by means of point sources. Measurement was made at each of three different doping agent contents.

Figure 22:
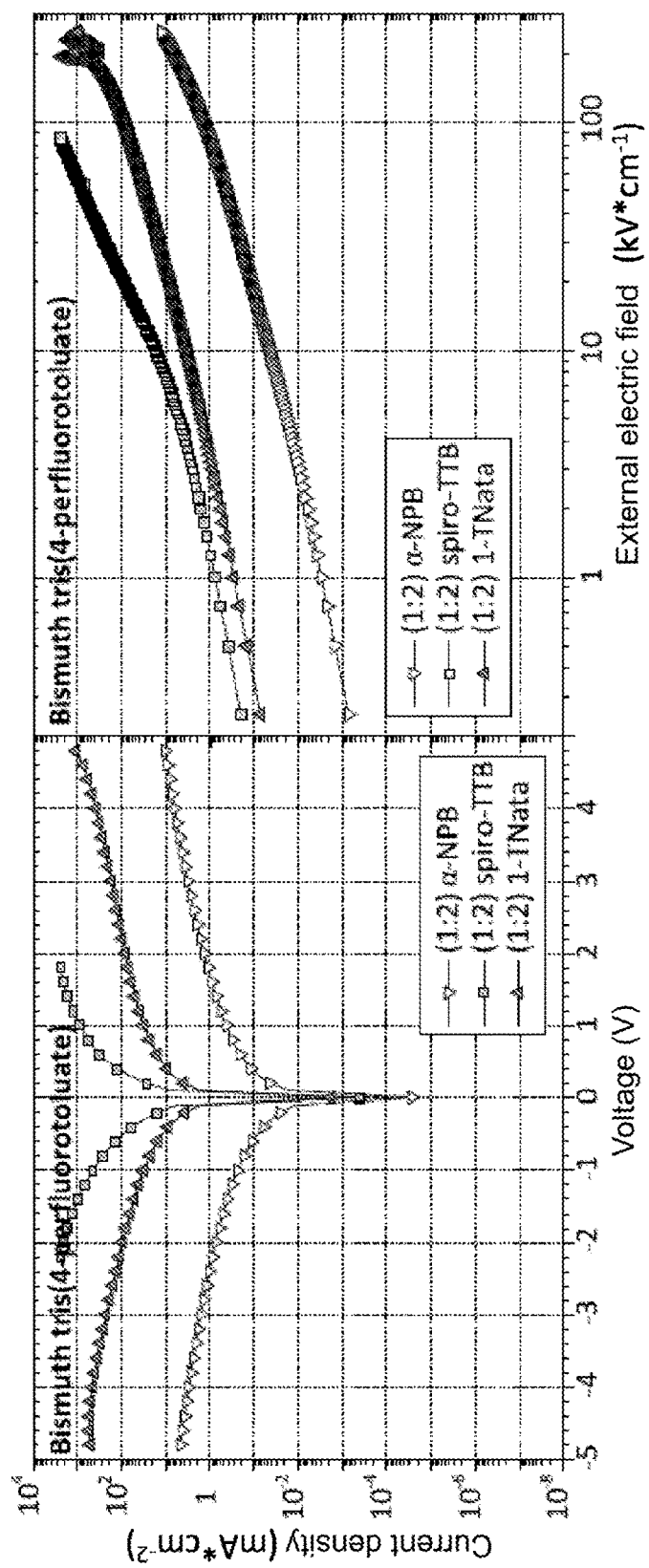
FIG. 22 shows, with regard to reference example VII, current density plotted against voltage and current density plotted against external field strength for the matrix materials 1-TNata, spiro-TTB and α-NPB doped with bismuth (III) tris(4-perfluorotoluate)

FIG. 22 shows with regard to reference example VII current density plotted against voltage and current density plotted against external field strength for the matrix materials 1-TNata, spiro-TTB and α-NPB doped with bismuth (III) tris(4-perfluorotoluate).

Figure 23:
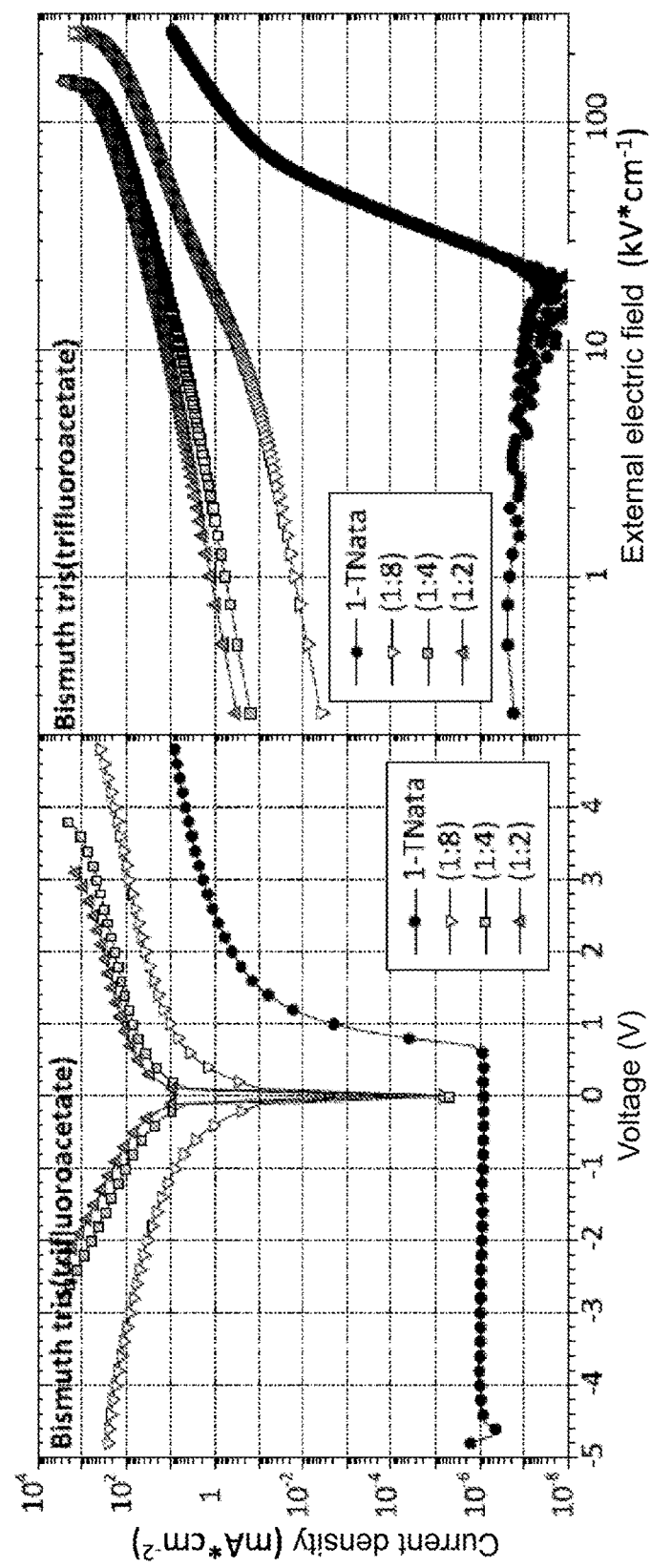
FIG. 23 shows, with regard to reference example VIII, current density plotted against voltage and current density plotted against external field strength for 1-TNata doped with bismuth(III) tris(trifluoroacetate) for the doped matrix material obtained by deposition by means of point sources.

FIG. 23 shows with regard to reference example VIII current density plotted against voltage and current density plotted against external field strength for 1-TNata doped with bismuth(III) tris(trifluoroacetate) for the doped matrix material obtained by deposition by means of point sources. Measurement was made at each of three different doping agent contents.

Figure 24:
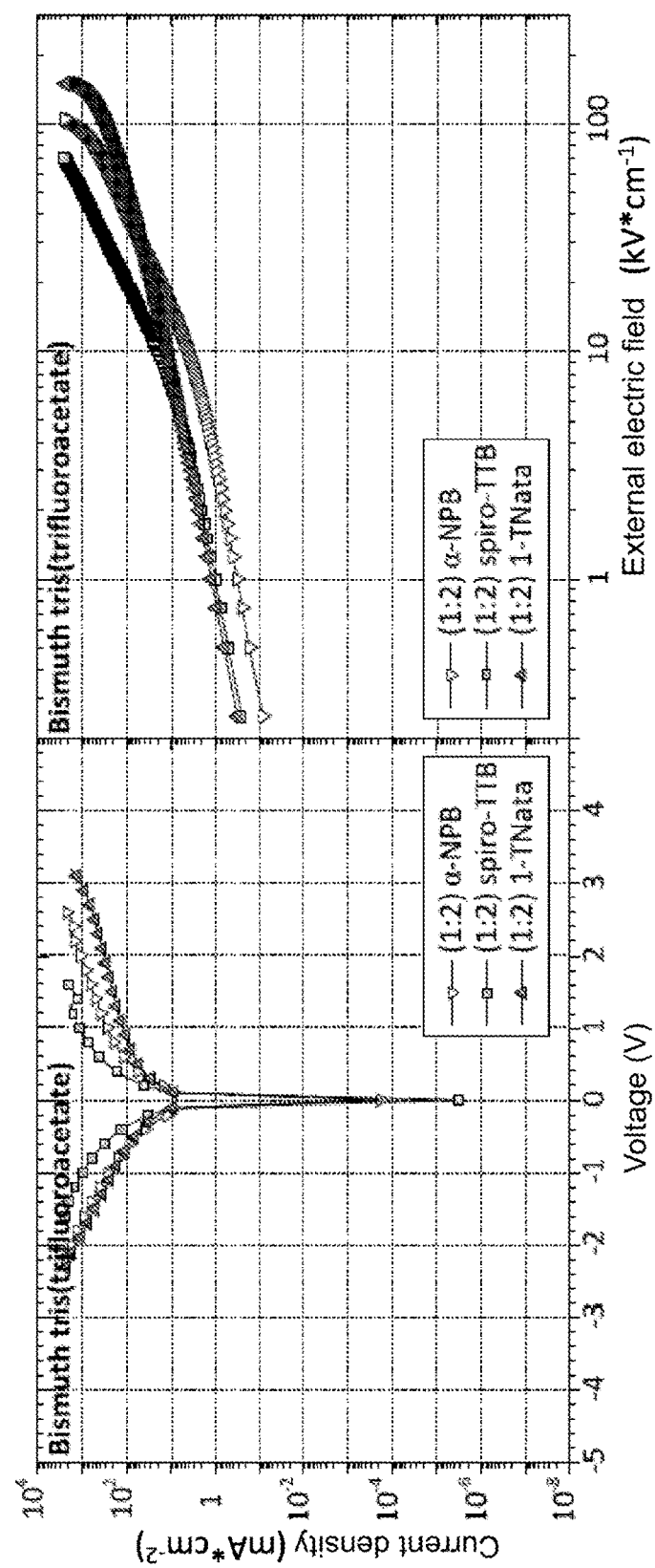
FIG. 24 shows, with regard to reference example VIII, current density plotted against voltage and current density plotted against external field strength for the matrix materials 1-TNata, spiro-TTB and α-NPB doped with bismuth (III) tris(trifluoroacetate)

FIG. 24 shows with regard to reference example VIII current density plotted against voltage and current density plotted against external field strength for the matrix materials 1-TNata, spiro-TTB and α-NPB doped with bismuth (III) tris(trifluoroacetate).

Figure 25:
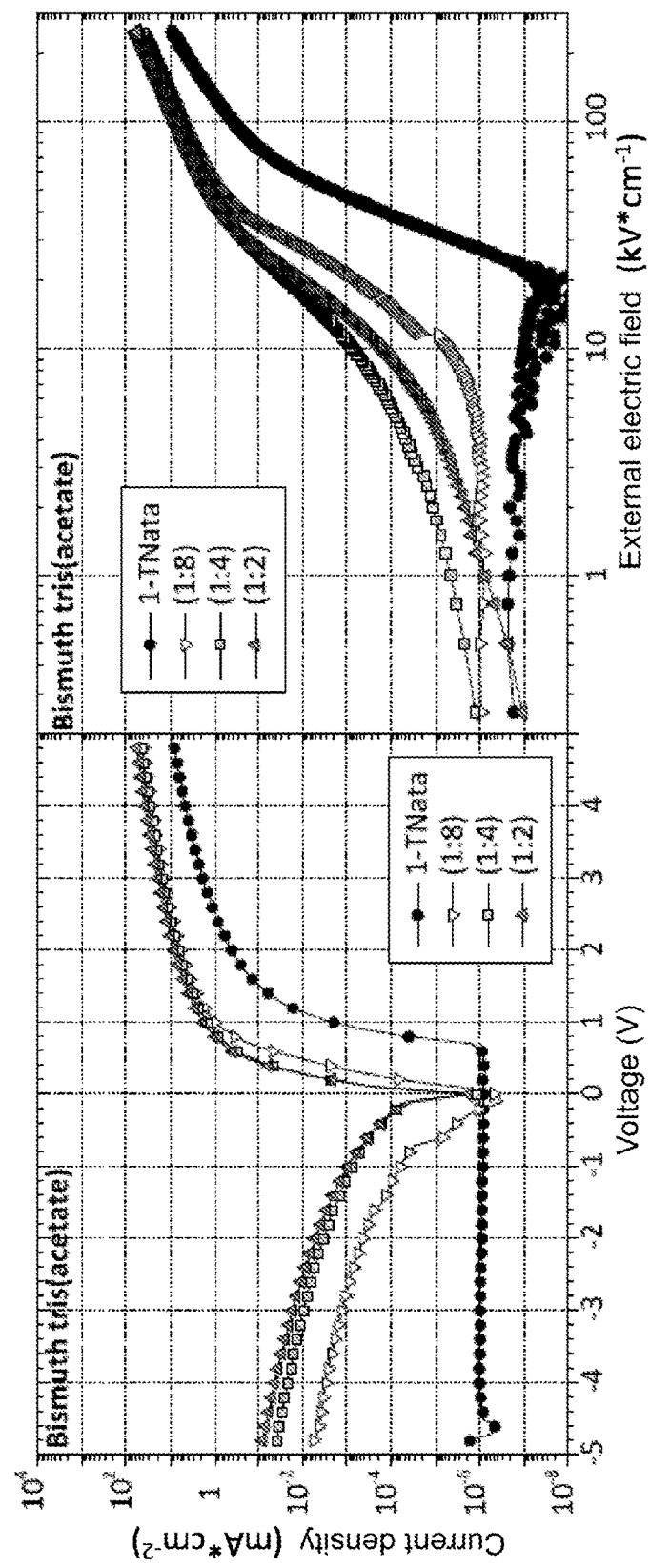
FIG. 25 shows, with regard to reference example IX, current density plotted against voltage and current density plotted against external field strength for 1-TNata doped with bismuth(III) tris(triacetate) for the doped matrix material obtained by deposition by means of point sources.

FIG. 25 shows with regard to reference example IX current density plotted against voltage and current density plotted against external field strength for 1-TNata doped with bismuth(III) tris(triacetate) for the doped matrix material obtained by deposition by means of point sources. Measurement was made at each of three different doping agent contents.

Figure 26:
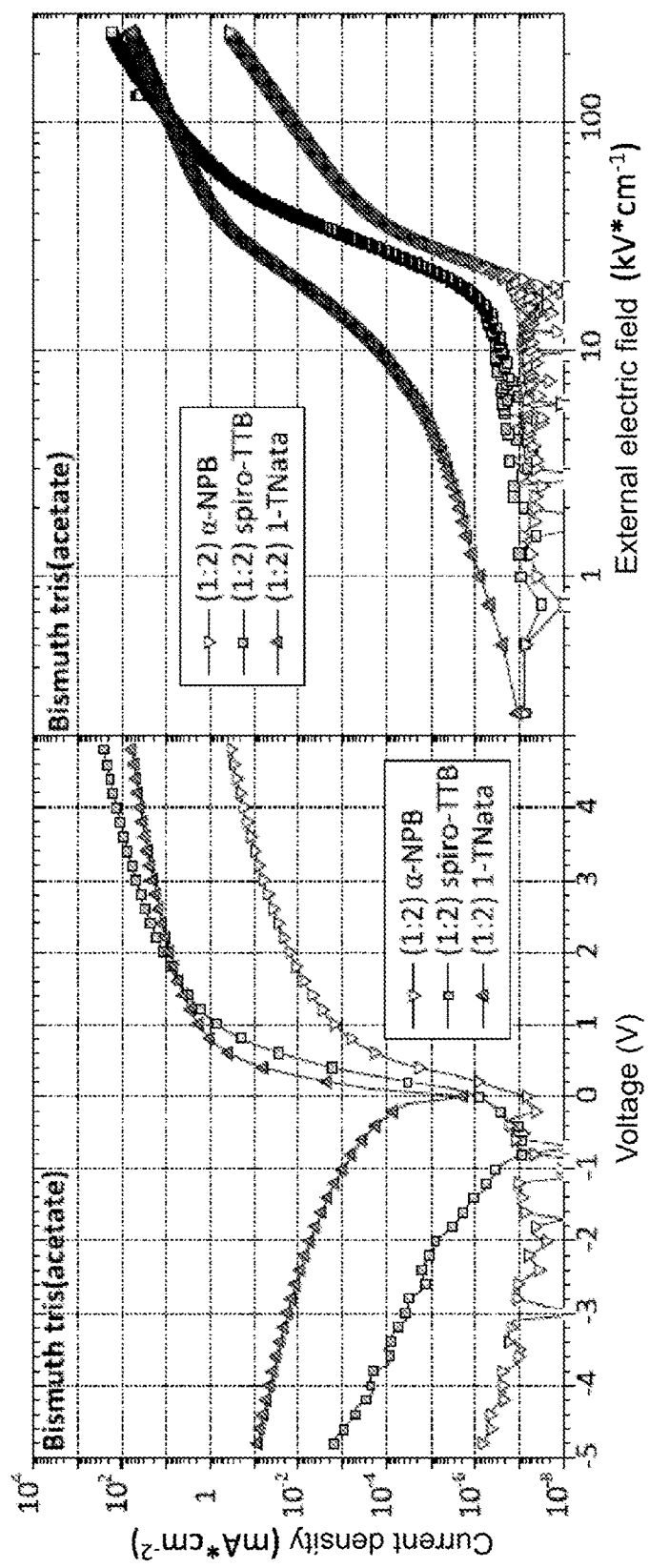
FIG. 26 shows, with regard to reference example IX, current density plotted against voltage and current density plotted against external field strength for the matrix materials 1-TNata, spiro-TTB and α-NPB doped with bismuth (III) tris(triacetate).

FIG. 26 shows with regard to reference example IX current density plotted against voltage and current density plotted against external field strength for the matrix materials 1-TNata, spiro-TTB and α-NPB doped with bismuth (III) tris(triacetate).

The two examples I and II will be presented below. The two metal complexes copper(I) bis-trifluoromethylbenzoate (example I) and bismuth(III) tris-3,5-trifluoromethylbenzoate (example II) are extraordinarily thermally stable with decomposition temperatures distinctly above the sublimation temperature thereof. Both complexes can be deposited by means of sources in which the complexes undergo collisions with at least one wall of the source. For example, both complexes have stability which is sufficiently high for gas-phase deposition via linear sources. This has been confirmed experimentally by "ampoule tests".

None of the further reference examples, namely reference examples I to IX, exhibited sufficient stability in ampoule tests. The inventors have established experimentally that these substances are not suitable for deposition by means of sources in which the complexes undergo collisions.

The electrical properties of the respective doped layers are likewise investigated below. Since each of the metal complexes of reference examples I to IX is not sufficiently stable for deposition by means of sources in which collisions occur with at least one wall of the source, measurements were made on organic electrical layers deposited via point sources and compared with one another. The complexes of reference examples I to IX, for example, are not sufficiently stable for deposition by means of linear sources.

Example I

Example I relates to the metal complex copper(I) bistrifluoromethylbenzoate, hereinafter abbreviated to Cu(3,5-tfmb).

In general, many copper(I) complexes of fluorinated benzoate derivatives may be produced in the following manner:

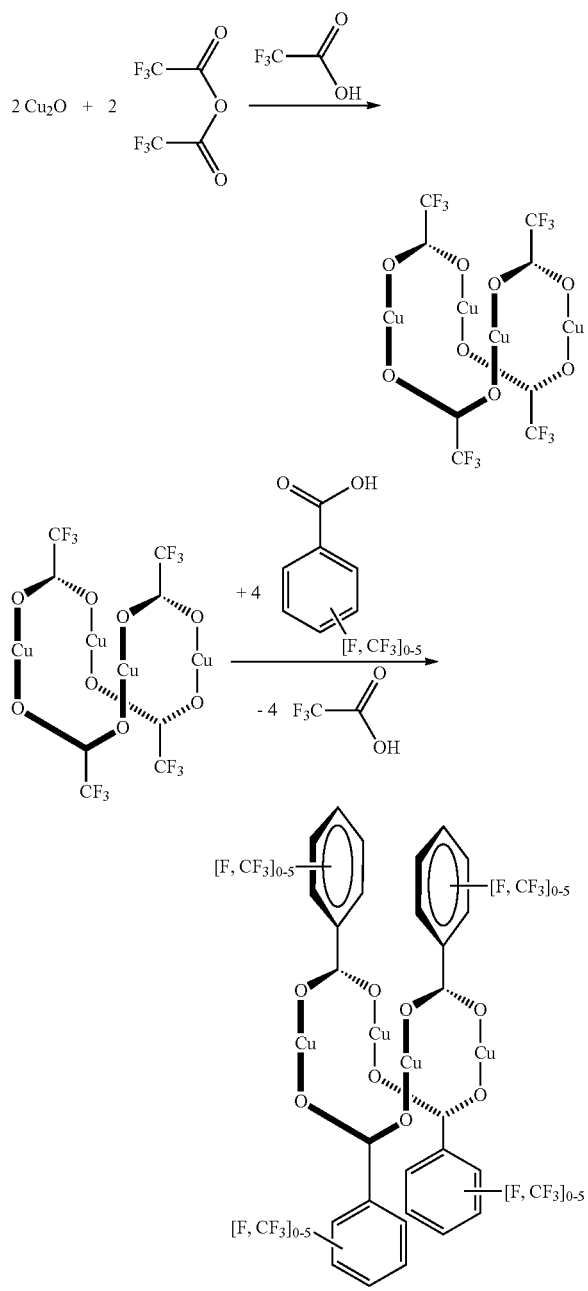

A multiplicity of the metal complexes used in the method according to the invention may be produced in similar manner.

The metal complex 3,5-bis-(trifluoromethylbenzoate) may for instance accordingly be obtained from Cu(I) trifluoroacetate in accordance with the following method:

5 g (7.08 mmol) Cu(I) trifluoroacetate is weighed out together with 7.5 g (29.03 mmol) 3,5-bis-(trifluoromethylbenzoic acid) in a 250 ml two-necked flask under inert gas (for example, in a glove box). The mixture is combined with 80 ml toluene and 70 ml benzene, giving rise to a greenish reaction solution. The latter is gently refluxed overnight (bath temperature approx. 90° C.), whereupon the solvent is removed by distillation. A grayish cream-colored product remains, which is dried under a vacuum. Yield is 6.98 g (76%) after single sublimation. The sublimation range of the substance is 160-180° C. at $2 \times 10^{-5}$ mbar.

It was possible to demonstrate by ampoule tests that Cu(3,5-tfmb) is stable up to at least 225° C.

In ampoule tests, approx. 100 to 500 mg of the substance to be investigated is melted at a base pressure of $10^{-5}$ to $10^{-6}$ mbar. The ampoule is then heated in an oven and kept at the respective temperature for approx. 100 hours. It is possible to recognize by visual inspection whether the metal complex has decomposed because decomposition leads to discoloration, frequently to a brown color. Finally, after around 100 hours at the first test temperature, the ampoule is further heated in 10-20 Kelvin steps and again left in the oven at the new test temperature for around 100 hours. The experiment is continued until it is finally possible to conclude that decomposition has occurred due to discoloration.

In addition, in a control experiment, in each case following the visual determination, a further ampoule containing a new sample of the same metal complex to be tested is again heated in the oven for around 100 hours. Heating here proceeds to a temperature just below the visually determined decomposition temperature. The sample treated in this manner is then investigated by elemental analysis and in this manner the stability of the complex is confirmed on the basis of the elemental composition.

For copper(I) bis-trifluoromethylbenzoate according to example I, ampoule tests were carried out for three different temperatures: 210° C., 230° C. and 240° C.

The measurements demonstrate that the complex is stable up to at least 225° C. This was confirmed by means of elemental analysis.

Cu(3,5-tfmb) is thus suitable for deposition from the gas phase also by means of sources in which the complex collides with at least one of the walls of the sources. Deposition from the gas phase via linear sources is possible, for example.

Layers doped with Cu(3,5-tfmb) have very good optical transparency in the visible range. Cu(3,5-tfmb) is additionally distinguished by sufficiently good doping agent strength.

As is furthermore shown by FIG. 6, organic layers doped with Cu(3,5-tfmb) have good conductivities.

Example II

Example II relates to a method according to the invention, wherein the metal complex is bismuth(III) tris-3,5-trifluoromethylbenzoate, hereinafter abbreviated to Bi(3,5-tfmb)$_3$.

Bismuth complexes according to example II and the metal complexes described below of reference examples I to VII were produced in accordance with the following general method according to scheme 1:

Scheme 1:

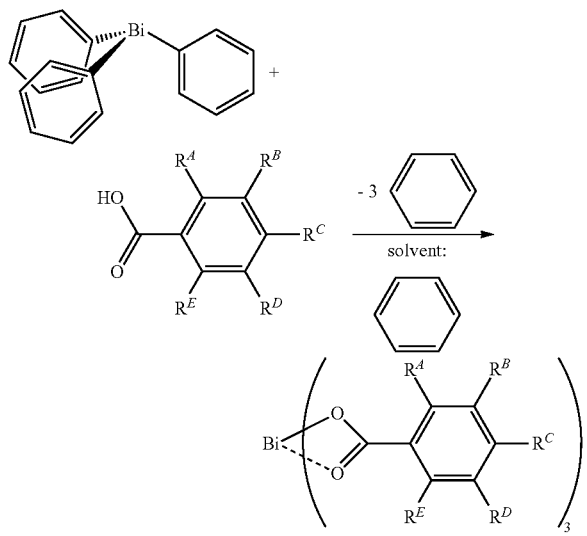

For Bi(3,5-tfmb)$_3$, residues $R^B$ and $R^D$, thus the residues in 3,5-position, are each CF$_3$ substituents and residues $R^A$, $R^C$ and $R^E$ are each hydrogen atoms.

After purification by means of sublimation, it was confirmed by elemental analysis that Bi(3,5-tfmb)$_3$ had been obtained (measured: carbon in % 33.5; hydrogen in % 0.5; calculated: carbon in % 330.06; hydrogen in % 0.92).

The thermal stability of bismuth(III) tris-3,5-trifluoromethylbenzoate was determined with the assistance of ampoule tests, as have already been described in connection with example I. According to said tests, the metal complex is stable at 330° C. even in the event of thermal treatment over an interval of time of 144 hours. No discoloration in the ampoule is to be observed at temperatures of below 330° C. Only from 330° C. does slight discoloration become visible. Elemental analysis data also confirm that, within the limits of statistical error, the complex is thermally stable up to 330° C.

As shown in table 1, similar tests were carried out in each case for 144 hours at the temperatures 260° C., 280° C., 315° C. and 330° C. Samples of the heat-treated substance were in each case investigated by means of elemental analysis, with the carbon content being determined. On the basis of the deviation of the carbon content determined in this manner from the expected carbon content of the undecomposed complex, it is possible to draw conclusions as to the degree of decomposition of the complex after the respective heat treatment. The inventors were able to demonstrate on the basis of the test series that bismuth(III) tris-3,5-trifluoromethylbenzoate according to example II has particularly high thermal stability and, taking account of statistical error, only exhibits clear signs of decomposition at temperatures of above 330° C.

TABLE 1

Determination of carbon content by means of elemental analysis at two different locations (location A and location B) of the ampoule on which substance has in each case been deposited after the ampoule test.

|  | Location A | Location B |
| --- | --- | --- |
| 3x sublimated material | no material | theoret. value + 0.44% C |
| 144 h at 260° C. | theoret. value + 0.49% C | theoret. value + 0.05% C |
| 144 h at 280° C. | theoret. value + 0.63% C | theoret. value + 0.12% C |
| 144 h at 300° C. | theoret. value + 0.49% C | no material |
| 144 h at 315° C. | theoret. value + 0.47% C | theoret. value + 0.18% C |
| 144 h at 330° C. | theoret. value + 0.14% C | decomposition |

The slight deviations of the determined carbon content up to temperatures of 330° C. from the theoretically calculated content (of 330.06%) demonstrate the high thermal stability of bismuth(III) tris-3,5-trifluoromethylbenzoate. Clear signs of decomposition of the complex are only observed at temperatures of above 330° C.

Elemental analysis thus confirms stability of the complex up to 330° C. taking account of statistical error.

Doping agents with fluorinated alkyl substituents $R^1$, as is apparent from the example of bismuth(III) tris-3,5-trifluoromethylbenzoate, are particularly suitable, thanks to their high thermal stability, for gas-phase deposition by means of sources in which the metal complexes, i.e., the dopants, undergo collisions with at least one wall of the source. For example, the metal complexes are sufficiently stable to be depositable from the gas phase via linear sources without decomposition.

Layers doped with Bi(3,5-tfmb)$_3$ layers have very good optical transparency in the visible range.

Bi(3,5-tfmb)$_3$ is additionally distinguished by sufficiently good doping agent strength. This is further clarified by the experimental data summarized below.

FIGS. 7 and 8 and tables 2 and 3 summarize the electrical properties of organic layers doped with Bi(3,5-tfmb)$_3$.

TABLE 2

Summary of the electrical properties of 1-TNata doped with Bi(3,5-tfmb)$_3$.
Electrical properties are in particular investigated on the matrix at three different doping agent contents (1:8, 1:4 and 1:2).

|  | (1:8) | (1:4) | (1:2) |
| --- | --- | --- | --- |
| Exp. molar ratio | 1/8.08 (7.64$_{vol.}$ %) | 1/4.07 (14.11$_{vol.}$ %) | 1/1.99 (25.14$_{vol.}$ %) |
| $\sigma_0$ (S · cm$^{-1}$) | 4.08 · 10$^{-7}$ (±1.00%) | 7.01 · 10$^{-7}$ (±4.61%) | 5.27 · 10$^{-7}$ (±0.88%) |
| $\rho_{c.;0}$ ($\Omega$ · cm$^{-2}$) | 1.96 · 10$^7$ (±5.65%) | 1.72 · 10$^6$ (±5.14%) | 4.64 · 10$^5$ (±3.86%) |
| $E_{bi}$ (kV · cm$^{-1}$) |  | <0.25 |  |
| $\varepsilon_r$ |  | Too conductive |  |
| r + 1 | 3.24 (±1.72%) | 2.33 (±4.61%) | 1.59 (±2.42%) |
| $\mu_0$ (cm$^2$ · V$^{-1}$ · s$^{-1}$) | 3.20 · 10$^{-5}$ (±25%)* | Ballistic |  |
| $\gamma$ (cm$^{1/2}$ · V$^{1/2}$) | 2.54 · 10$^{-4}$ (±4.9%)* |  |  |

The electrical properties for the various materials shown in table 2 and all the further tables were determined by measurements made on 200 nm thick organic layers supported on ITO (indium tin oxide) substrates and obtained by coevaporation via point sources.

"Exp. molar ratio" here in each case denotes the molar ratio of matrix material and the metal complex. "$\sigma_o$" denotes the conductivity of the measured organic electronic layer. "$\rho_{C;o}$" denotes the contact resistance. "$E_{bi}$" denotes the electrical field strength of the internal electrical field of the semiconductor material ("built-in electric field"; this field strength is obtained from the difference in the work function between anode and cathode of the organic electronic component). "$\in_r$" indicates the dielectric constant of the material obtained by coevaporation.

A series of further parameters was determined in connection with the transport regime of the charge carriers in the organic electrical layer, as are described in various theories of conductivity in the literature. "r" here denotes an empirical factor ("trap distribution factor") which describes an exponential distribution in accordance with the charge carrier transport models (Steiger et al. "Energetic trap distributions in organic semiconductors" Synthetic Metals 2002, 129 (1), 1-7; Schwoerer et al. "Organic Molecular Solids", Wiley-VCH, 2007). "$\mu_o$" denotes charge carrier mobility and $\gamma$ denotes the field-activation factor. $\gamma$ is for instance of significance in connection with a description of charge transport according to the Murgatroyd equation: Murgatroyd, P. N. "Theory of space-charge-limited current enhanced by Frenkel effect" Journal of Physics D: Applied Physics 1979, 3 (2), 151.

The terms "too conductive", "ballistic", "no ohmic contact", "trapping", "aging", "no TFLC", "compliance" used in tables 2 to 31 in each case have the following meanings: "Too conductive" means that the measurement is not meaningful due to excessively high layer conductivity. "No ohmic contact" indicates that no electrical contact was present. "Compliance" indicates that the preset current limitation of the measuring instrument was achieved. "TFLC" denotes "trap-filled limited regime" in accordance with the stated papers by Steiger et al. and Schwoerer et al. and refers to a transport regime for the charge carriers of the organic electrical layer. The terms "ballistic", "trapping" and "aging" here refer to further transport regimes in accordance with the various models of conductivity described in the literature. The various conductivity regimes may here be recognized from the exponent of current-voltage dependency.

The respective abbreviations also apply similarly for tables 3 to 21.

TABLE 3

Summary of the electrical properties of matrix materials 1-TNata, α-NPB and spiro-TTB doped with (1:2) Bi(3,5-tfmb)$_3$. The electrical properties when doping different matrix materials are compared.

| | 1-TNata | α-NPB | spiro-TTB |
|---|---|---|---|
| Exp. molar ratio | 1/1.99 (25.14$_{vol.}$ %) | 1/1.99 (35.32$_{vol.}$ %) | 1/2.00 (19.99$_{vol.}$ %) |
| $\sigma_0$ (S · cm$^{-1}$) | 5.27 · 10$^{-7}$ (±0.88%) | 1.05 · 10$^{-7}$ (±1.23%) | 4.60 · 10$^{-6}$ (±0.63%) |
| $\rho_{c;0}$ (Ω · cm$^{-2}$) | 4.64 · 10$^5$ (±3.86%) | 3.55 · 10$^8$ (±7.18%) | 4.76 · 10$^5$ (±4.76%) |
| $E_{bi}$ (kV · cm$^{-1}$) | | <0.25 | |
| $\varepsilon_r$ | Too conductive | 2.15 (±5.07%) | Too conductive |
| r + 1 | 1.59 (±2.42%) | 3.15 (±3.71%) | 2.24 (±3.01%) |
| $\mu_0$ (cm$^2$ · V$^{-1}$ · s$^{-1}$) | Ballistic | 5.28 · 10$^{-5}$ (±37.3%) | Ballistic |
| $\gamma$ (cm$^{1/2}$ · V$^{1/2}$) | | 1.88 · 10$^{-6}$ (±11.4%) | |

The measurements confirm that matrix materials doped with Bi(3,5-tfmb)$_3$ have good electrical properties, in particular sufficiently good conductivities.

This is clarified below by a comparison with the electrical properties of a multiplicity of further complexes which, in contrast with Cu(3,5-tfmb) according to example I and Bi(3,5-tfmb)$_3$ according to example II, did not exhibit sufficient thermal stability in ampoule tests and are therefore not suitable for deposition from the gas phase by means of sources in which collisions occur with at least one wall of the source.

Reference Example I

Reference example I relates to the use of bismuth(III) tris(2,6-difluorobenzoate), abbreviated to Bi(2,6-dfb)$_3$, as a metal complex for gas-phase deposition.

Bi(2,6-dfb)$_3$ was synthesized in accordance with scheme 1. For Bi(2,6-dfb)$_3$, residues R$^A$ and R$^E$ in scheme 1 are in each case fluorine atoms and the remaining substituents R$^B$, R$_C$ and R$^D$ in each case hydrogen atoms.

After purification by means of sublimation, it was confirmed by elemental analysis that Bi(2,6-tfmb)$_3$ had been obtained (measured: carbon in % 36.2; hydrogen in % 1.5; calculated: carbon in % 370.06; hydrogen in % 1.32).

FIGS. 9 and 10 and tables 4 and 5 summarize the electrical properties of organic layers doped with Bi(2,6-dfb)$_3$.

TABLE 4

Summary of the electrical properties of 1-TNata doped with Bi(2,6-dfb)$_3$.

|  | (1:8) | (1:4) | (1:2) |
|---|---|---|---|
| Exp. molar ratio | 1/8.07 (4.57$_{vol.}$ %) | 1/3.96 (8.90$_{vol.}$ %) | 1/2.00 (16.22$_{vol.}$ %) |
| $\sigma_0$ (S · cm$^{-1}$) | 6.98 · 10$^{-8}$ (±2.18%) | 3.62 · 10$^{-8}$ (±2.56%) | 4.80 · 10$^{-8}$ (±1.25%) |
| $\rho_{c;0}$ (Ω · cm$^{-2}$) |  | no ohmic contact |  |
| $E_{bi}$ (kV · cm$^{-1}$) | 13.6 (±19.3%) | 12.3 (±12.2%) | 9.50 (±13.2%) |
| $\varepsilon_r$ | 2.48 (±4.21%) | 2.45 (±11.9%) | 3.51 (±53.2%) |
| r + 1 | 15.2 (±6.60%) | 13.3 (±6.80%) | 12.1 (±6.11%) |
| $\mu_0$ (cm$^2$ · V$^{-1}$ · s$^{-1}$) | 4.82 · 10$^{-6}$ (±8.71%) | 3.18 · 10$^{-6}$ (±16.6%) | 3.95 · 10$^{-6}$ (±58.2%) |
| $\gamma$ (cm$^{1/2}$ · V$^{1/2}$) | 2.01 · 10$^{-3}$ (±0.81%) | 1.78 · 10$^{-3}$ (±0.89%) | 9.82 · 10$^{-4}$ (±1.23%) |

TABLE 5

Summary of the electrical properties of matrix materials 1-TNata, α-NPB and spiro-TTB doped with (1:2) Bi(2,6-dfb)$_3$.

|  | 1-TNata | α-NPB | spiro-TTB |
|---|---|---|---|
| Exp. molar ratio | 1/2.00 (16.22$_{vol.}$ %) | 1/2.02 (23.72$_{vol.}$ %) | 1/1.96 (12.87$_{vol.}$ %) |
| $\sigma_0$ (S · cm$^{-1}$) | 4.08 · 10$^{-8}$ (±1.25%) | 4.89 · 10$^{-9}$ (±2.82%) | 2.04 · 10$^{-7}$ (±1.90%) |
| $\rho_{c;0}$ (Ω · cm$^{-2}$) |  | no ohmic contact |  |
| $E_{bi}$ (kV · cm$^{-1}$) | 9.50 (±13.2%) | 30.0 (±9.17%) | 12.5 (±46.0%) |
| $\varepsilon_r$ | 3.51 (±53.2%) | 2.34 (±3.83%) | 3.01 (±5.83%) |
| r + 1 | 12.1 (±6.11%) | 22.5 (±54.9%) | 17.0 (±4.08%) |
| $\mu_0$ (cm$^2$ · V$^{-1}$ · s$^{-1}$) | 3.95 · 10$^{-6}$ (±58.2%) | 7.09 · 10$^{-7}$ (±8.73%) | 1.45 · 10$^{-5}$ (±9.65%) |
| $\gamma$ (cm$^{1/2}$ · V$^{1/2}$) | 9.82 · 10$^{-4}$ (±1.23%) | 4.94 · 10$^{-3}$ (±1.27%) | 4.33 · 10$^{-3}$ (±0.78%) |

Reference Example II

Reference example II relates to the use of bismuth(III) tris(4-fluorobenzoate), abbreviated to Bi(4-fb)$_3$, as a metal complex for gas-phase deposition.

Bi(4-fb)$_3$ was synthesized in accordance with scheme 1. For Bi(4-fb)$_3$, the residues R$^A$, R$^B$, R$^D$ and R$^E$ in scheme 1 are hydrogen atoms and only R$^C$ is a fluorine atom.

After purification by means of sublimation, it was confirmed by elemental analysis that Bi(4-fb)$_3$ had been obtained (measured: carbon in % 42.4; hydrogen in % 2.3; calculated: carbon in % 40.26; hydrogen in % 1.92).

FIGS. 11 and 12 and tables 6 and 7 summarize the electrical properties of organic layers doped with Bi(4-fb)$_3$.

TABLE 6

Summary of the electrical properties of 1-TNata doped with Bi(4-fb)$_3$.

|  | (1:8) | (1:4) | (1:2) |
|---|---|---|---|
| Exp. molar ratio | 1/8.09 (4.54$_{vol.}$ %) | 1/4.02 (8.74$_{vol.}$ %) | 1/1.99 (16.20$_{vol.}$ %) |
| $\sigma_0$ (S · cm$^{-1}$) | 2.33 · 10$^{-7}$ (±1.60%) | 1.62 · 10$^{-7}$ (±1.80%) | 2.50 · 10$^{-7}$ (±1.21%) |
| $\rho_{c;0}$ (Ω · cm$^{-2}$) |  | no ohmic contact | 3.80 · 10$^8$ (±9.84%) |
| $E_{bi}$ (kV · cm$^{-1}$) | 6.38 (±64.7%) | 3.13 (±100%) | <0.25 |
| $\varepsilon_r$ | 2.75 (±2.63%) | 2.52 (±16.4%) | 2.91 (±9.61%) |
| r + 1 | 18.5 (±8.97%) | 9.02 (±2.62%) | 5.40 (±2.05%) |
| $\mu_0$ (cm$^2$ · V$^{-1}$ · s$^{-1}$) | 3.74 · 10$^{-5}$ (±7.51%) | 1.19 · 10$^{-5}$ (±21.5%) | 3.30 · 10$^{-5}$ (±15.4%) |
| $\gamma$ (cm$^{1/2}$ · V$^{1/2}$) | 2.45 · 10$^{-3}$ (±1.15%) | 1.59 · 10$^{-3}$ (±0.93%) | 1.12 · 10$^{-4}$ (±6.68%) |

TABLE 7

Summary of the electrical properties of matrix materials 1-TNata, α-NPB and spiro-TTB doped with (1:2) Bi(4-fb)$_3$.

|  | 1-TNata | α-NPB | spiro-TTB |
|---|---|---|---|
| Exp. molar ratio | 1/1.99 (16.20$_{vol.}$ %) | 1/2.01 (23.74$_{vol.}$ %) | 1/1.97 (12.74$_{vol.}$ %) |
| $\sigma_0$ (S · cm$^{-1}$) | 2.50 · 10$^{-7}$ (±1.21%) | 5.72 · 10$^{-7}$ (±1.11%) | 1.99 · 10$^{-6}$ (±0.81%) |
| $\rho_{c;0}$ (Ω · cm$^{-2}$) | 3.80 · 10$^8$ (±9.84%) | no ohmic contact |  |
| $E_{bi}$ (kV · cm$^{-1}$) | <0.25 |  | 7.75 (±80.7%) |
| $\varepsilon_r$ | 2.91 (±9.61%) | 2.36 (±7.06%) | 3.32 (±7.14%) |
| r + 1 | 5.40 (±2.05%) | 7.23 (±17.06%) | 13.7 (±2.08%) |

TABLE 7-continued

Summary of the electrical properties of matrix materials
1-TNata, α-NPB and spiro-TTB doped with (1:2) Bi(4-fb)₃.

|  | 1-TNata | α-NPB | spiro-TTB |
|---|---|---|---|
| $\mu_0$ (cm² · V⁻¹ · s⁻¹) | $3.30 \cdot 10^{-5}$ (±15.4%) | Trapping | Aging |
| $\gamma$ (cm^{1/2} · V^{1/2}) | $1.12 \cdot 10^{-4}$ (±6.68%) |  |  |

Reference Example III

Reference example III relates to the use of bismuth(III) tris(3-fluorobenzoate), abbreviated to Bi(3-fb)₃, as a metal complex for gas-phase deposition.

Bi(3-fb)₃ was synthesized in accordance with scheme 1. For Bi(3-fb)₃, the residues $R^A$, $R^C$, $R^D$ and $R^E$ in scheme 1 are hydrogen atoms and only $R^B$ is a fluorine atom.

After purification by means of sublimation, it was confirmed by elemental analysis that Bi(3-fb)₃ had been obtained (measured: carbon in % 390.2; hydrogen in % 2.3; calculated: carbon in % 40.26; hydrogen in % 1.92).

FIGS. 13 and 14 and tables 8 and 9 summarize the electrical properties of organic layers doped with Bi(3-fb)₃.

TABLE 8

Summary of the electrical properties of 1-TNata doped with Bi(3-fb)₃.

|  | (1:8) | (1:4) | (1:2) |
|---|---|---|---|
| Exp. molar ratio | 1/8.16 (4.62 vol. %) | 1/3.97 (9.07 vol. %) | 1/1.94 (16.92 vol. %) |
| $\sigma_0$ (S · cm⁻¹) | $1.73 \cdot 10^{-7}$ (±1.51%) | $1.48 \cdot 10^{-7}$ (±0.96%) | $1.38 \cdot 10^{-7}$ (±1.27%) |
| $\rho_{c;\,0}$ (Ω · cm⁻²) | no ohmic contact | | $9.07 \cdot 10_8$ (±9.56%) |
| $E_{bi}$ (kV · cm⁻¹) | 8.38 (±25.4%) | 0.63 (±100%) | <0.25 |
| $\varepsilon_r$ | 3.57 (±35.5%) | 3.22 (±9.91%) | 3.64 (±6.24%) |
| r + 1 | 12.5 (±3.23%) | 6.22 (±1.90%) | 4.67 (±2.12%) |
| $\mu_0$ (cm² · V⁻¹ · s⁻¹) | $9.07 \cdot 10^{-6}$ (±40.2%) | $7.52 \cdot 10^{-6}$ (±14.8%) | $3.37 \cdot 10^{-6}$ (±11.6%) |
| $\gamma$ (cm^{1/2} · V^{1/2}) | $1.52 \cdot 10^{-3}$ (±1.04%) | $1.36 \cdot 10^{-3}$ (±1.19%) | $1.95 \cdot 10^{-3}$ (±1.13%) |

TABLE 9

Summary of the electrical properties of matrix materials
1-TNata, α-NPB and spiro-TTB doped with (1:2) Bi(3-fb)₃.

|  | 1-TNata | α-NPB | spiro-TTB |
|---|---|---|---|
| Exp. molar ratio | 1/1.94 (16.92 vol. %) | 1/2.05 (23.85 vol. %) | 1/2.00 (12.86 vol. %) |
| $\sigma_0$ (S · cm⁻¹) | $1.38 \cdot 10^{-7}$ (±1.27%) | $6.10 \cdot 10^{-8}$ (±0.88%) | $1.69 \cdot 10^{-6}$ (±0.87%) |
| $\rho_{c;\,0}$ (Ω · cm⁻²) | $9.07 \cdot 10^{8}$ (±9.56%) | no ohmic contact | $1.35 \cdot 10^{4}$ (±1.70%) |
| $E_{bi}$ (kV · cm⁻¹) | <0.25 | 21.38 (±13.5%) | <0.25 |
| $\varepsilon_r$ | 3.64 (±6.24%) | 2.62 (±7.18%) | 2.97 (±15.7%) |
| r + 1 | 4.67 (±2.12%) | 17.0 (±16.9%) | no TFLC |
| $\mu_0$ (cm² · V⁻¹ · s⁻¹) | $3.37 \cdot 10^{-6}$ (±11.6%) | Trapping | Aging |
| $\gamma$ (cm^{1/2} · V^{1/2}) | $1.95 \cdot 10^{-3}$ (±1.13%) |  |  |

Reference Example IV

Reference example IV relates to the use of bismuth(III) tris(3,5-difluorobenzoate), abbreviated to Bi(3,5-dfb)₃, as a metal complex for gas-phase deposition.

Bi(3,5-dfb)₃ was synthesized in accordance with scheme 1. For Bi(3,5-dfb)₃, residues $R^A$, $R^C$ and $R^E$ in scheme 1 are in each case hydrogen atoms and substituents $R^B$ and $R^D$ are in each case fluorine atoms.

After purification by means of sublimation, it was confirmed by elemental analysis that Bi(3,5-dfb)₃ had been obtained (measured: carbon in % 36.3; hydrogen in % 1.4; calculated: carbon in % 370.06; hydrogen in % 1.32).

FIGS. 15 and 16 and tables 10 and 11 summarize the electrical properties of organic layers doped with Bi(3,5-dfb)₃.

TABLE 10

Summary of the electrical properties of 1-TNata doped with Bi(3,5-dfb)3.

|  | (1:8) | (1:4) | (1:2) |
|---|---|---|---|
| Exp. molar ratio | 1/8.01 (4.77 vol. %) | 1/3.93 (9.25 vol. %) | 1/196 (17.01 vol. %) |
| $\sigma_0$ (S · cm⁻¹) | $4.27 \cdot 10^{-7}$ (± 1.03%) | $2.81 \cdot 10^{-7}$ (±0.66%) | $2.97 \cdot 10^{-7}$ (±1.31%) |
| $\rho_{c;\,0}$ (Ω · cm⁻²) | $2.07 \cdot 10^{9}$ (±8.50%) | $5.12 \cdot 10^{7}$ (±8.73%) | $1.43 \cdot 10^{6}$ (±4.98%) |
| $E_{bi}$ (kV · cm⁻¹) |  | <0.25 |  |
| $\varepsilon_r$ | 2.67 (±7.01%) | 2.60 (±9.36%) | 2.69 (±10.8%) |
| r + 1 | 6.46 (±2.28%) | 3.75 (±3.36%) | 1.56 (±1.90%) |
| $\mu_0$ (cm² · V⁻¹ · s⁻¹) | $3.14 \cdot 10^{-5}$ (±11.9%) | Ballistic |  |
| $\gamma$ (cm^{1/2} · V^{1/2}) | $5.09 \cdot 10^{-4}$ (±1.16%) |  |  |

TABLE 11

Summary of the electrical properties of matrix materials 1-TNata,
α-NPB and spiro-TTB doped with (1:2) Bi(3,5-dfb)₃.

|  | 1-TNata | α-NPB | spiro-TTB |
|---|---|---|---|
| Exp. molar ratio | 1/1.96 (17.01 vol. %) | 1/1.99 (24.64 vol. %) | 1/2.00 (13.05 vol. %) |
| $\sigma_0$ (S · cm⁻¹) | $2.97 \cdot 10^{-7}$ (±1.31%) | $7.18 \cdot 10^{-7}$ (±1.90%) | $4.40 \cdot 10^{-6}$ (±1.73%) |
| $\rho_{c;\,0}$ (Ω · cm⁻²) | $1.43 \cdot 10^{6}$ (±4.98%) | no ohmic contact | $2.91 \cdot 10^{5}$ (±3.76%) |
| $E_{bi}$ (kV · cm⁻¹) | <0.25 | 12.75 (±35.3%) | <0.25 |
| $\varepsilon_r$ | 2.69 (±10.8%) | 2.35 (±3.84%) | Too conductive |
| r + 1 | 1.56 (±1.90%) | 12.9 (±21.4%) | no TFLC |
| $\mu_0$ (cm² · V⁻¹ · s⁻¹) | Ballistic | Trapping | Aging |
| $\gamma$ (cm^{1/2} · V^{1/2}) |  |  |  |

Reference Example V

Reference example V relates to the use of bismuth(III) tris(3,4,5-trifluorobenzoate), abbreviated to Bi(3,4,5-tfb)₃, as a metal complex for gas-phase deposition.

Bi(3,4,5-tfb)₃ was synthesized in accordance with scheme 1. For Bi(3,4,5-tfb)₃, residues $R^A$ and $R^E$ in scheme 1 are in each case hydrogen atoms and the remaining substituents $R^B$, $R^C$ and $R^D$ are in each case fluorine atoms.

After purification by means of sublimation, it was confirmed by elemental analysis that Bi(3,4,5-tfb)₃ had been obtained (measured: carbon in % 330.8; hydrogen in % 1.2; calculated: carbon in % 34.33; hydrogen in % 0.82).

FIGS. 17 and 18 and tables 12 and 13 summarize the electrical properties of organic layers doped with Bi(3,4,5-tfb)$_3$.

TABLE 12

Summary of the electrical properties of 1-TNata doped with Bi(3,4,5-tfb)$_3$.

|  | (1:8) | (1:4) | (1:2) |
|---|---|---|---|
| Exp. molar ratio | 1/8.15 | 1/3.92 | 1/1.96 |
|  | (5.59 $_{vol.}$ %) | (10.97 $_{vol.}$ %) | (19.73 $_{vol.}$ %) |
| $\sigma_0$ (S·cm$^{-1}$) | 6.45·10$^{-7}$ | 9.73·10$^{-7}$ | 1.09·10$^{-6}$ |
|  | (±1.00%) | (±0.88%) | (±0.76%) |
| $\rho_{c.;\,0}$ (Ω·cm$^{-2}$) | 3.24·10$^7$ | 1.21·10$^6$ | 1.78·10$^5$ |
|  | (±6.25%) | (±5.02%) | (±4.25%) |
| $E_{bi}$ (kV·cm$^{-1}$) |  | <0.25 |  |
| $\varepsilon_r$ |  | Too conductive |  |
| r + 1 | 4.12 | 2.22 | 1.48 |
|  | (±2.46%) | (±1.78%) | (±2.46%) |
| $\mu_0$ (cm$^2$·V$^{-1}$·s$^{-1}$) | 6.13·10$^{-5}$ | Ballistic |  |
|  | (±25%)* |  |  |
| $\gamma$ (cm$^{1/2}$·V$^{1/2}$) | 5.28·10$^{-4}$ |  |  |
|  | (±1.6%)* |  |  |

TABLE 13

Summary of the electrical properties of matrix materials 1-TNata, α-NPB and spiro-TTB doped with (1:2) Bi(3,4,5-tfb)$_3$.

|  | 1-TNata | α-NPB | spiro-TTB |
|---|---|---|---|
| Exp. molar ratio | 1/1.96 | 1/2.00 | 1/2.01 |
|  | (19.73 $_{vol.}$ %) | (28.22 $_{vol.}$ %) | (15.23 $_{vol.}$ %) |
| $\sigma_0$ (S·cm$^{-1}$) | 1.09·10$^{-6}$ | 1.77·10$^{-6}$ | 1.19·10$^{-5}$ |
|  | (±0.76%) | (±1.68%) | (±0.94%) |
| $\rho_{c.;\,0}$ (Ω·cm$^{-2}$) | 1.78·10$^5$ | 5.39·10$^7$ | 2.06·10$^5$ |
|  | (±4.25%) | (±8.77%) | (±5.68%) |
| $E_{bi}$ (kV·cm$^{-1}$) |  | <0.25 |  |
| $\varepsilon_r$ | Too conductive | 2.26 | Too conductive |
|  |  | (±12.2%) |  |
| r + 1 | 1.48 | 3.28 | 3.28 |
|  | (±2.46%) | (±2.22%) | (±3.72%) |
| $\mu_0$ (cm$^2$·V$^{-1}$·s$^{-1}$) | Ballistic | 9.39·10$^{-6}$ | 3.37·10$^{-3}$ |
|  |  | (±19.1%) | (±23%)* |
| $\gamma$ (cm$^{1/2}$·V$^{1/2}$) |  | 3.42·10$^{-3}$ | 2.01·10$^{-4}$ |
|  |  | (±3.90%) | (±3.1%)* |

Reference Example VI

Reference example VI relates to the use of bismuth(III) tris(perfluorobenzoate), abbreviated to Bi(pfb)$_3$, as a metal complex for gas-phase deposition.

Bi(pfb)$_3$ was synthesized in accordance with scheme 1. For Bi(pfb)$_3$, all five residues $R^A$ to $R^E$ in scheme 1 are in each case fluorine atoms.

After purification by means of sublimation, it was confirmed by elemental analysis that Bi(pfb)$_3$ had been obtained (measured: carbon in % 29.9 (6); calculated: carbon in % 29.93). FIGS. 19 and 20 and tables 14 and 15 summarize the electrical properties of organic layers doped with Bi(pfb)$_3$.

TABLE 14

Summary of the electrical properties of 1-TNata doped with Bi(pfb)$_3$.

|  | (1:8) | (1:4) | (1:2) |
|---|---|---|---|
| Exp. molar ratio | 1/8.08 | 1/3.98 | 1/1.97 |
|  | (5.18 $_{vol.}$ %) | (9.98 $_{vol.}$ %) | (18.28 $_{vol.}$ %) |
| $\sigma_0$ (S·cm$^{-1}$) | 9.81·10$^{-7}$ | 2.65·10$^{-6}$ (±1.73%) | 6.06·10$^{-6}$ |
|  | (±1.62%) |  | (±1.28%) |

TABLE 14-continued

Summary of the electrical properties of 1-TNata doped with Bi(pfb)$_3$.

|  | (1:8) | (1:4) | (1:2) |
|---|---|---|---|
| $\rho_{c.;\,0}$ (Ω·cm$^{-2}$) | 4.27·10$^6$ | 9.88·10$^4$ | 8.26·10$^3$ |
|  | (±6.35%) | (±3.41%) | (±2.96%) |
| $E_{bi}$ (kV·cm$^{-1}$) |  | <0.25 |  |
| $\varepsilon_r$ | 2.92 | Too conductive |  |
|  | (±4.86%) |  |  |
| r + 1 | 3.76 | 2.00 | no TFLC |
|  | (±4.99%) | (±2.34%) |  |
| $\mu_0$ (cm$^2$·V$^{-1}$·s$^{-1}$) |  | Ballistic |  |
| $\gamma$ (cm$^{1/2}$·V$^{1/2}$) |  |  |  |

TABLE 15

Summary of the electrical properties of matrix materials 1-TNata, α-NPB and spiro-TTB dope with (1:2) Bi(pfb)$_3$.

|  | 1-TNata | α-NPB | spiro-TTB |
|---|---|---|---|
| Exp. molar ratio | 1/1.97 | 1/2.00 | 1/1.88 |
|  | (18.28 $_{vol.}$ %) | (26.38 $_{vol.}$ %) | (14.90 $_{vol.}$ %) |
| $\sigma_0$ (S·cm$^{-1}$) | 6.06·10$^{-6}$ | 2.78·10$^{-6}$ | 9.52·10$^{-5}$ |
|  | (±1.28%) | (±0.96%) | (±1.40%) |
| $\rho_{c.;\,0}$ (Ω·cm$^{-2}$) | 8.26·10$^3$ | 1.37·10$^8$ | 1.92·10$^4$ |
|  | (±2.96%) | (±8.22%) | (±3.24%) |
| $E_{bi}$ (kV·cm$^{-1}$) |  | <0.25 |  |
| $\varepsilon_r$ | Too conductive | 2.43 | Too conductive |
|  |  | (±7.17%) |  |
| r + 1 | no TFLC | 4.97 | 2.98 |
|  |  | (±2.34%) | (±1.77%) |
| $\mu_0$ (cm$^2$·V$^{-1}$·s$^{-1}$) | Ballistic | 4.88·10$^{-5}$ | Compliance |
|  |  | (±10.5%) |  |
| $\gamma$ (cm$^{1/2}$·V$^{1/2}$) |  | 1.14·10$^{-3}$ |  |
|  |  | (±0.84%) |  |

Reference Example VII

Reference example VII relates to the use of bismuth(III) tris(4-perfluorotoluate), abbreviated to Bi(4-pftl)$_3$, as a metal complex for gas-phase deposition.

For Bi(4-pftl)$_3$, residues $R^A$, $R^B$, $R^D$ and $R^E$ in scheme 1 are in each case fluorine atoms and $R^C$ is a CF$_3$ group.

After purification by means of sublimation, it was confirmed by elemental analysis that Bi(4-pftl)$_3$ had been obtained (measured: carbon in % 30.0; calculated: carbon in % 29.03).

FIGS. 21 and 22 and tables 16 and 17 summarize the electrical properties of organic layers doped with Bi(4-pftl)$_3$.

TABLE 16

Summary of the electrical properties of 1-TNata doped with Bi(4-pftl)$_3$.

|  | (1:8) | (1:4) | (1:2) |
|---|---|---|---|
| Exp. molar ratio | 1/8.10 | 1/4.02 | 1/1.97 |
|  | (5.63 $_{vol.}$ %) | (10.75 $_{vol.}$ %) | (19.68 $_{vol.}$ %) |
| $\sigma_0$ (S·cm$^{-1}$) | 1.07·10$^{-6}$ | 2.62·10$^{-6}$ | 4.13·10$^{-6}$ |
|  | (±0.81%) | (±0.89%) | (±1.20%) |
| $\rho_{c.;\,0}$ (Ω·cm$^{-2}$) | 9.30·10$^5$ | 2.31·10$^5$ | 3.83·10$^4$ |
|  | (±3.67%) | (±3.03%) | (±2.85%) |
| $E_{bi}$ (kV·cm$^{-1}$) |  | <0.25 |  |
| $\varepsilon_r$ |  | Too conductive |  |
| r + 1 | 2.44 | 1.77 | no TFLC |
|  | (±29.0%) | (±2.86%) |  |
| $\mu_0$ (cm$^2$·V$^{-1}$·s$^{-1}$) |  | Ballistic |  |
| $\gamma$ (cm$^{1/2}$·V$^{1/2}$) |  |  |  |

TABLE 17

Summary of the electrical properties of matrix materials 1-TNata, α-NPB and spiro-TTB doped with (1:2) Bi(4-pftl)$_3$.

|  | 1-TNata | α-NPB | spiro-TTB |
|---|---|---|---|
| Exp. molar ratio | 1/1.97 | 1/2.04 | 1/2.03 |
|  | (19.68 $_{vol.}$ %) | (27.82 $_{vol.}$ %) | (15.13 $_{vol.}$ %) |
| $\sigma_0$ (S · cm$^{-1}$) | 4.13 · 10$^{-6}$ | 3.20 · 10$^{-6}$ | 1.53 · 10$^{-4}$ |
|  | (±1.20%) | (±0.84%) | (±1.02%) |
| $\rho_{c;\,0}$ (Ω · cm$^{-2}$) | 3.83 · 10$^4$ | 3.41 · 10$^6$ | 1.25 · 10$^4$ |
|  | (±2.85%) | (±3.72%) | (±3.93%) |
| $E_{bi}$ (kV · cm$^{-1}$) |  | <0.25 |  |
| $\varepsilon_r$ | Too conductive | 2.10 | // |
|  |  | (±27.4%) |  |
| r + 1 | no TFLC | 1.42 | 2.52 |
|  |  | (±2.07%) | (±2.27%) |
| $\mu_0$ (cm$^2$ · V$^{-1}$ · s$^{-1}$) | Ballistic |  | Compliance |
| $\gamma$ (cm$^{1/2}$ · V$^{1/2}$) |  |  |  |

Further conventional metal complexes with acetate- and trifluoroacetate-based ligands were also used by the inventors for comparison with the complexes used in the method according to the invention:

Reference Example VIII

Reference example VIII relates to the use of bismuth(III) tris(trifluoroacetate), abbreviated to Bi(tfa)$_3$, as a metal complex for gas-phase deposition. Production is described in the literature (for example, Suzuki, H.; Matano, Y. in Organobismuth Chemistry, Elsevier 2001).

FIGS. 23 and 24 and tables 18 and 19 summarize the electrical properties of organic layers doped with Bi(tfa)$_3$.

TABLE 18

Summary of the electrical properties of 1-TNata doped with Bi(tfa)$_3$.

|  | (1:8) | (1:4) | (1:2) |
|---|---|---|---|
| Exp. molar ratio | 1/8.24 | 1/3.92 | 1/1.97 |
|  | (2.37 $_{vol.}$ %) | (4.85 $_{vol.}$ %) | (9.22 $_{vol.}$ %) |
| $\sigma_0$ (S · cm$^{-1}$) | 2.06 · 10$^{-6}$ | 4.47 · 10$^{-6}$ | 7.53 · 10$^{-6}$ |
|  | (±0.95%) | (±1.23%) | (±1.21%) |
| $\rho_{c;\,0}$ (Ω · cm$^{-2}$) | 6.82 · 10$^5$ | 2.10 · 10$^4$ | 9.40 · 10$^3$ |
|  | (±3.31%) | (±2.34%) | (±2.50%) |
| $E_{bi}$ (kV · cm$^{-1}$) |  | <0.25 |  |
| $\varepsilon_r$ |  | Too conductive |  |
| r + 1 | 2.45 | no TFLC | no TFLC |
|  | (±1.50%) |  |  |
| $\mu_0$ (cm$^2$ · V$^{-1}$ · s$^{-1}$) | After TFLC, the slope decreases |||
| $\gamma$ (cm$^{1/2}$ · V$^{1/2}$) | to a limit new 3/2 (ballistic). |||
|  | Just before exponentially increasing (aging) |||

"After TFLC, the slope decreases to a limit near 3/2 (ballistic)" and "Just before exponentially increasing (aging)" refers to a transition from one charge transport regime to another.

TABLE 19

Summary of the electrical properties of matrix materials 1-TNata, α-NPB and spiro-TTB doped with (1:2) Bi(tfa)$_3$.

|  | 1-TNata | α-NPB | spiro-TTB |
|---|---|---|---|
| Exp. molar ratio | 1/1.97 | 1/1.96 | 1/1.97 |
|  | (9.22 $_{vol.}$ %) | (14.21 $_{vol.}$ %) | (7.05 $_{vol.}$ %) |
| $\sigma_0$ (S · cm$^{-1}$) | 7.53 · 10$^{-6}$ | 3.97 · 10$^{-5}$ | 2.28 · 10$^{-4}$ |
|  | (±1.21%) | (±0.94%) | (±0.79%) |
| $\rho_{c;\,0}$ (Ω · cm$^{-2}$) | 9.40 · 10$^3$ | 3.80 · 10$^4$ | 1.05 · 10$^4$ |
|  | (±2.50%) | (±2.13%) | (±3.03%) |
| $E_{bi}$ (kV · cm$^{-1}$) |  | <0.25 |  |

TABLE 19-continued

Summary of the electrical properties of matrix materials 1-TNata, α-NPB and spiro-TTB doped with (1:2) Bi(tfa)$_3$.

|  | 1-TNata | α-NPB | spiro-TTB |
|---|---|---|---|
| $\varepsilon_r$ |  | Too conductive |  |
| r + 1 | no TFLC | 2.50 | 2.58 |
|  |  | (±2.54%) | (±2.99%) |
| $\mu_0$ (cm$^2$ · V$^{-1}$ · s$^{-1}$) | Ballistic | Aging ||
| $\gamma$ (cm$^{1/2}$ · V$^{1/2}$) |  |  |  |

It is apparent from the data that complexes with unfluorinated ligands also dope, but distinctly worse than complexes with fluorinated ligands. These complexes, like the other reference examples, are likewise unsuitable for sources in which collisions occur with at least one wall of the source.

Reference Example IX

Reference example IX relates to the use of bismuth(III) tris(triacetate), abbreviated to Bi(ac)$_3$, as a metal complex for gas-phase deposition. The complex is commercially obtainable.

FIGS. 25 and 26 and tables 20 and 21 summarize the electrical properties of organic layers doped with Bi(ac)$_3$.

TABLE 20

Summary of the electrical properties of 1-TNata doped with Bi(ac)$_3$.

|  | (1:8) | (1:4) | (1:2) |
|---|---|---|---|
| Exp. molar ratio | 1/8.16 | 1/4.20 | 1/2.03 |
|  | (1.46 $_{vol.}$ %) | (2.80 $_{vol.}$ %) | (5.64 $_{vol.}$ %) |
| $\sigma_0$ (S · cm$^{-1}$) | 4.31 · 10$^{-7}$ | 4.06 · 10$^{-7}$ | 6.13 · 10$^{-7}$ |
|  | (±1.90%) | (±0.86%) | (±0.81%) |
| $\rho_{c;\,0}$ (Ω · cm$^{-2}$) | no ohmic contact | 8.41 · 10$^8$ | 5.07 · 10$^9$ |
|  |  | (±9.79%) | (±9.63%) |
| $E_{bi}$ (kV · cm$^{-1}$) | 3.13 | <0.25 ||
|  | (±100%) |  |  |
| $\varepsilon_r$ | 2.67 | 2.10 | 2.78 |
|  | (±37.3%) | (±10.4%) | (±6.88%) |
| r + 1 | 9.87 | 5.70 | 7.31 |
|  | (±2.98%) | (±2.73%) | (±1.24%) |
| $\mu_0$ (cm$^2$ · V$^{-1}$ · s$^{-1}$) | 2.81 · 10$^{-5}$ | 5.12 · 10$^{-5}$ | 4.46 · 10$^{-5}$ |
|  | (±42.0%) | (±15.1%) | (±11.8%) |
| $\gamma$ (cm$^{1/2}$ · V$^{1/2}$) | 1.29 · 10$^{-3}$ | 3.19 · 10$^{-4}$ | 6.76 · 10$^{-4}$ |
|  | (±0.80%) | (±1.88%) | (±1.33%) |

TABLE 21

Summary of the electrical properties of matrix materials 1-TNata, α-NPB and spiro-TTB doped with (1:2) Bi(ac)$_3$.

|  | 1-TNata | α-NPB | spiro-TTB |
|---|---|---|---|
| Exp. molar ratio | 1/2.03 | 1/1.99 | 1/2.05 |
|  | (5.64 $_{vol.}$ %) | (8.99 $_{vol.}$ %) | (4.23 $_{vol.}$ %) |
| $\sigma_0$ (S · cm$^{-1}$) | 6.13 · 10$^{-7}$ | 6.10 · 10$^{-10}$ | 1.68 · 10$^{-7}$ |
|  | (±0.81%) | (±16.0%) | (±8.76%) |
| $\rho_{c;\,0}$ (Ω · cm$^{-2}$) | 5.07 · 10$^9$ | no ohmic contact ||
|  | (±9.63%) |  |  |
| $E_{bi}$ (kV · cm$^{-1}$) | <0.25 | 16.3 | 18.4 |
|  |  | (±10.8%) | (±12.9%) |
| $\varepsilon_r$ | 2.78 | 2.06 | 2.76 |
|  | (±6.88%) | (±5.58%) | (±4.44%) |
| r + 1 | 7.31 | 11.9 | 13.0 |
|  | (±1.24%) | (±12.7%) | (±3.18%) |
| $\mu_0$ (cm$^2$ · V$^{-1}$ · s$^{-1}$) | 4.46 · 10$^{-5}$ | Trapping ||
|  | (±11.8%) |  |  |
| $\gamma$ (cm$^{1/2}$ · V$^{1/2}$) | 6.76 · 10$^{-4}$ |  |  |
|  | (±1.33%) |  |  |

The majority of the stated examples, example I and example II and most of the reference examples, have sufficiently good doping agent strengths. Matrix materials doped with these complexes exhibit sufficiently good electrical conductivities in the case of examples I and II and also of many reference examples.

However, with regard to the stability, in particular the thermal stability, of the complex, only the metal complexes of example I and example II meet the elevated requirements for deposition by means of sources in which the complex collides with at least one wall of the source. In contrast, none of the complexes of the reference examples exhibited sufficient stability in order to be deposited from the gas phase by means of sources in which collisions occur with walls of the source.

For example, only the complexes of example I and example II, but not the complexes of the reference examples, can be deposited by means of linear sources. While all the complexes are sufficiently stable for deposition by means of point sources, only those complexes with at least one substituent $R^1$ thus meet the high stability requirements.

The individual combinations of constituents and the features of the embodiments which have already been mentioned serve by way of example; exchanging and replacing such teaching with other teaching provided in the present document, including the cited documents, is likewise explicitly considered. A person skilled in the art will recognize that variations, modifications and other embodiments which are described here may likewise occur without deviating from or going beyond the concept and the scope of the invention.

The above-stated description should accordingly be considered to be exemplary rather than limiting. The word "comprise" used in the claims does not exclude other constituents or steps. The indefinite article "a" does not exclude a plural meaning. The mere fact that certain measurements are recited in different claims does not mean that a combination of these measurements might not advantageously be used. The scope of the invention is defined in the following claims, and the associated equivalents.

The invention claimed is:

1. A method for producing an organic electronic component, wherein the component comprises at least one organic electronic layer comprising a matrix containing a dopant, the method comprising:
   depositing the dopant of the at least one organic electronic layer by a gas-phase deposition via a source, wherein the source is configured such that the dopant undergoes collisions with at least one wall of the source and the dopant is a metal complex comprising at least one metal atom M and at least one ligand L attached to the metal atom M, wherein the ligand L has the following structure:

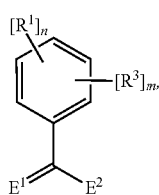

wherein $E^1$ and $E^2$ are mutually independently selectable to be oxygen, sulfur, selenium, NH or NR', wherein R' is selected from the group consisting of alkyl and aryl and are attachable to a substituted benzene ring of the ligand L,
   wherein the substituents $R^1$ are mutually independently selected from branched or unbranched, fluorinated aliphatic hydrocarbons with 1 to 10 C atoms, wherein n=1 to 5,
   wherein substituents $R^2$ are mutually independently selected from CN, branched or unbranched aliphatic hydrocarbons with 1 to 10 C atoms, aryl or heteroaryl, and
   wherein m=0 to at most 5−n.

2. The method according to claim 1, wherein the metal atom M of is selected from the group consisting of Cu, Cr, Mo, Rh and Ru.

3. The method according to claim 1, wherein the metal atom M is selected from the group consisting of Bi and Cu.

4. The method according to claim 1, wherein at least one of the substituents $R^1$ is a —$CF_3$ group.

5. The method according to claim 1, wherein the ligand L comprises precisely two substituents $R^1$, each forming a —$CF_3$ group.

6. The method according to claim 1, wherein the ligand L comprises precisely two substituents $R^1$, each forming a —$CF_3$ group and each being arranged in 3,5-position on the benzene ring of the ligand L.

7. The method according to claim 1, wherein the substituents $R^2$ are mutually independently selectable from the group consisting of methyl, ethyl, n-propyl, iso-propyl, n-butyl, iso-butyl, tert-butyl and substituted and unsubstituted phenyl.

8. The method according to claim 1, wherein both $E^1$ and $E^2$ are oxygen.

9. The method according to claim 1, wherein the ligand L is selected from the group consisting of:

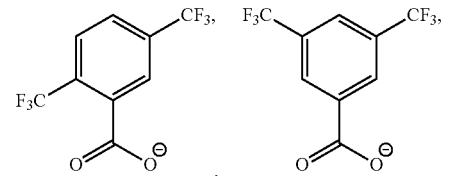

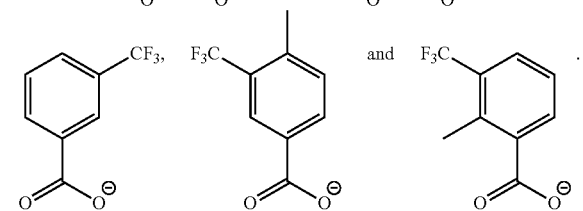

10. The method according to claim 1, wherein the metal complex is a bismuth complex, and wherein the ligand L has the following structure:

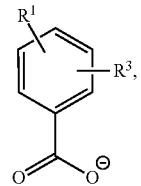

wherein the substituent R$^1$ is selected from branched or unbranched, fluorinated aliphatic hydrocarbons with 1 to 10 C atoms, and wherein substituent R$^3$ is selected from branched or unbranched fluorinated or unfluorinated aliphatic hydrocarbons with 1 to 10 C atoms, aryl or heteroaryl.

11. The method according to claim 1, wherein the metal complex has a decomposition temperature which is greater than 10 Kelvin above a sublimation temperature of the metal complex.

12. The method according to claim 1, wherein the metal complex has a decomposition temperature which is greater than 40 Kelvin above a sublimation temperature of the metal complex.

13. The method according to claim 1, wherein the metal complex has a decomposition temperature which is greater than 70 Kelvin above a sublimation temperature of the metal complex.

14. The method according to claim 1, wherein the source is a linear source.

15. A method for producing an organic electronic component, wherein the component comprises at least one organic electronic layer comprising a matrix containing a dopant, the method comprising:

depositing the dopant of the at least one organic electronic layer by a gas-phase deposition via a source, wherein the source is configured such that the dopant undergoes collisions with at least one wall of the source and the dopant is a metal complex comprising at least one metal atom M and at least one ligand L attached to the metal atom M, wherein the ligand L has the following structure:

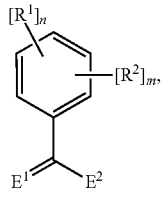

wherein E$^1$ and E$^2$ are mutually independently selectable to be oxygen, sulfur, selenium, NH or NR', wherein R' is selected from the group consisting of alkyl and aryl and are attachable to a substituted benzene ring of the ligand L, wherein the substituents R$^1$ are mutually independently selected from branched or unbranched, fluorinated aliphatic hydrocarbons with 1 to 10 C atoms, wherein n=1 to 5, wherein substituents R$^2$ are mutually independently selected from —CN, branched or unbranched aliphatic hydrocarbons with 1 to 10 C atoms, aryl or heteroaryl, wherein m=0 to at most 5-n, and wherein the metal atom M is selected from the group consisting of Bi, Cu, Cr, Mo, Rh and R.

16. The method according to claim 15, wherein the metal atom M is Bi.

17. The method according to claim 15, wherein the metal atom M is Bi in an oxidation state III.

18. The method according to claim 15, wherein the substituent R$^1$ is an at least difluorinated substituent.

19. The method according to claim 15, wherein the substituent R$^1$ is a perfluorinated substituent.

20. The method according to claim 15, wherein the substituent R$^1$ is a —CF$_3$ group and the metal atom M is Bi.

21. A method for producing an organic electronic component, wherein the component comprises at least one organic electronic layer comprising a matrix containing a dopant, the method comprising:

depositing the dopant of the at least one organic electronic layer by a gas-phase deposition via a source, wherein the source is configured such that the dopant undergoes collisions with at least one wall of the source, and wherein the dopant is a metal complex having the following structure:

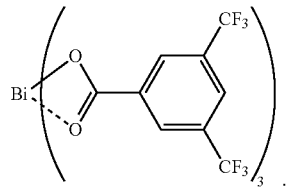

* * * * *

UNITED STATES PATENT AND TRADEMARK OFFICE
CERTIFICATE OF CORRECTION

PATENT NO. : 11,040,988 B2
APPLICATION NO. : 15/515735
DATED : June 22, 2021
INVENTOR(S) : Schmid et al.

Page 1 of 1

It is certified that error appears in the above-identified patent and that said Letters Patent is hereby corrected as shown below:

In the Claims

In Claim 1, Column 33; Lines 55-65 delete "$|R^3|$" and insert --$|R^2|$--

In Claim 2, Column 34; Line 14 delete "M of is" and insert --M is--

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*